United States Patent [19]

Alvarez et al.

[11] Patent Number: 5,912,179
[45] Date of Patent: Jun. 15, 1999

[54] METHOD FOR DETERMINING A LEVEL OF OXIDATIVE STRESS OF A TISSUE SAMPLE

[75] Inventors: Juan G. Alvarez, Boston; Mark Modell, Brookline, both of Mass.

[73] Assignee: Beth Israel Deaconess Medical Center, Inc., Boston, Mass.

[21] Appl. No.: 09/013,449

[22] Filed: Jan. 26, 1998

Related U.S. Application Data

[62] Division of application No. 08/294,173, Aug. 22, 1994, Pat. No. 5,712,165.

[51] Int. Cl.$^6$ .................................................. G01N 33/50
[52] U.S. Cl. .............................. 436/63; 436/64; 436/71; 436/171; 436/173; 250/910; 356/301; 600/310; 600/323; 600/473; 600/475; 600/476; 600/477; 600/478
[58] Field of Search ................................ 436/63, 64, 71, 436/171, 173; 250/910; 356/301; 600/473, 476, 477, 478, 310, 323, 435

[56] References Cited

U.S. PATENT DOCUMENTS

| | | | |
|---|---|---|---|
| 4,105,800 | 8/1978 | Jahns et al. | 426/231 |
| 4,226,540 | 10/1980 | Barten et al. | 356/237 |
| 4,253,848 | 3/1981 | Porter | 426/231 |
| 4,384,206 | 5/1983 | Bjarno | 436/21 |
| 4,515,165 | 5/1985 | Carroll | 128/664 |
| 4,764,258 | 8/1988 | Kauffman | 436/61 |
| 4,802,761 | 2/1989 | Bowen et al. | 356/301 |
| 4,900,680 | 2/1990 | Miyazawa | 436/71 |
| 4,912,050 | 3/1990 | Fossel | 436/64 |
| 4,930,516 | 6/1990 | Alfano et al. | 128/665 |
| 5,024,816 | 6/1991 | Arai et al. | 426/231 |
| 5,036,853 | 8/1991 | Jeffcoat et al. | 128/634 |
| 5,042,494 | 8/1991 | Alfano | 128/665 |
| 5,054,487 | 10/1991 | Clarke | 128/633 |
| 5,086,822 | 2/1992 | Kanda | 356/326 |
| 5,131,398 | 7/1992 | Alfano et al. | 128/665 |
| 5,161,531 | 11/1992 | Parsons et al. | 128/634 |
| 5,192,264 | 3/1993 | Fossel | 604/4 |
| 5,207,715 | 5/1993 | Fossel | 128/653.2 |
| 5,213,101 | 5/1993 | Fossel | 128/653.2 |
| 5,222,496 | 6/1993 | Clarke et al. | 128/633 |
| 5,239,180 | 8/1993 | Clarke | 250/339 |
| 5,239,258 | 8/1993 | Kauffman | 436/20 |
| 5,246,004 | 9/1993 | Clarke | 128/633 |
| 5,261,405 | 11/1993 | Fossel | 128/653.2 |
| 5,318,023 | 6/1994 | Vari et al. | 128/633 |
| 5,362,652 | 11/1994 | McClain | 436/164 |
| 5,377,676 | 1/1995 | Vari et al. | 128/634 |
| 5,395,755 | 3/1995 | Thorpe et al. | 436/172 |

FOREIGN PATENT DOCUMENTS

| | | |
|---|---|---|
| 0221642 | 5/1987 | European Pat. Off. . |
| 4278459 | 10/1992 | Japan . |
| 1809381 | 10/1991 | U.S.S.R. . |
| 2029015 | 3/1980 | United Kingdom . |
| 9321517 | 10/1993 | WIPO . |

OTHER PUBLICATIONS

Akira et al (1993), "Profiling of Arachidonic Acid Metabolites in Rabbit Platelets by Radio Gas Chromatography" *LIPIDS* 28:361–364.

Carney et al. (1993), "Near–Infrared Spectrophotometric Monitoring of Stroke–Related Changes in the Protein and Lipid Composition of Whole Gerbil Brains" *Anal Chem.* 65: 1305–1313.

(List continued on next page.)

*Primary Examiner*—Jill Warden
*Assistant Examiner*—Sharidan Carrillo
*Attorney, Agent, or Firm*—Lahive & Cockfield, LLP

[57] ABSTRACT

Systems and methods for material analysis are disclosed in which an organic sample (e.g., a foodstuff, tissue sample or petroleum product) is illuminated at a plurality of discrete wavelengths which are absorbed by fatty acid and fatty acid oxidation products in the sample. Measurements of the intensity of reflected or absorbed light at such wavelengths are taken, and a analysis of absorbance ratios for various wavelengths is performed. Changes in the reflection ratios are correlated with the oxidative state of fatty acids present in the material.

7 Claims, 16 Drawing Sheets

OTHER PUBLICATIONS

Dommes et al. (1976) "Structure Determination of Polyunsaturated Fatty Acids By Gas Chromatography–Mass Spectrometry—A Comparison of Fragmentation Patterns of Various Derivatives" *J of Chromatographic Science* 14: 360–366.

Duran et al. (1993), "Diagnosis of mitochondrial fatty acid oxidation defects" *Paediatr. Paedol 28* 19–25.

Esterbauer (1993), "Cytotoxicity and genotoxicity of lipid–oxidation products" *Am J Clin Nutr 57* 779S–786S.

Frankel et al. (1992), "Headspace Gas Chromatography to Determine Human Low Density Lipoprotein Oxidation" *LIPIDS 27* No. 12 1047–1051.

Ginsberg et al. (1988), "Peroxidative Damage to Cell Membranes Following Cerebral Ischemia A Cause of Ischemic Brain Injury?" *Neurochemical Pathology 9* 171–193.

Goddu (1957) "Determination of Unsaturation by Near–Infrared Spectrophotometry" *Analytical Chemistry 29* No. 12 1790–1794.

Gray (1978) "Measurement of Lipid Oxidation: A Review" *J. American Oil Chemists' Society 55*: 539–546.

Kubow (1993), "Lipid Oxidation Products in Food and Atherogenesis" *Nutrition Reviews 51* No. 2: 33–40.

Mizuno (1992), "Near–infrared FT–Raman spectra of the rat brain tissue" *Neuroscience Letters 141*: 47–52.

Ng (1983), "Identification of long chain dicarboxylic acids in the serum of two patients with Reye's Syndrome" *J of Chromatography 276*: 1–10.

Sergent et al. "Ultaviolet and Infrared Spectroscopy for Microdetermination of Oxidized and Unoxidized Fatty Acyl Esters in Cells" *Analytical Biochemistry 211*: 219–223.

Valenzuela (1991), "The biological significance of malondialdehyde determination in the assessment of tissue oxidative stress" *Life Sciences 48* 301–309.

Kubow "Routes of formation and toxic consequences of lipid oxidation products in food" Free Radical Biology & Medicine 12, 63–81, 1992.

Frenkel, "Lipid Oxidation: Mechanisms, Products & Biological Significance" JAOCS 61 No. 12, 1908–1917, 1984.

Buettner, "The Pecking Order of Free Radicals & AntiOxidants: Lipid Peroxidation, –Tocoplerol and Ascorbole" Archives of Biochemistry & Biophysics 300, No. 2, 535–543, 1993.

Buettner (1993), "The Pecking Order of Frea Radicals & Antioxidants: Lipid Peroxidation, –Tocopherol, & Ascorbale Archives of Biochemistry & Biophysics" 300 No. 2, pp. 535–543.

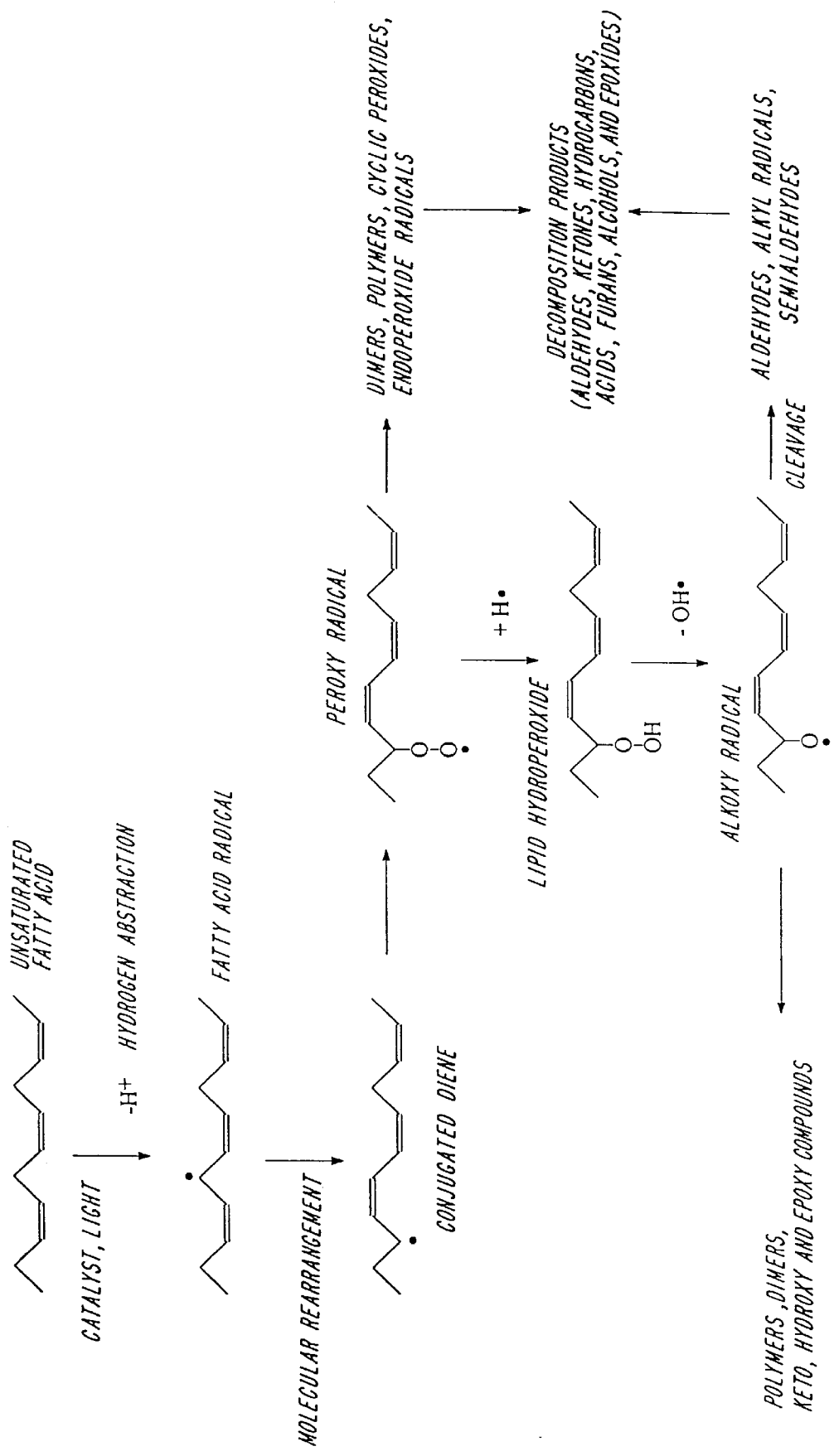

METHOD FOR DETERMINING A LEVEL OF OXIDATIVE STRESS OF A TISSUE SAMPLE

This application is a divisional application of Ser. No. 08/294,173 filed on Aug. 22, 1994, issued as U.S. Pat. No. 5,712,165 on Jan. 27, 1998. The contents of all of the aforementioned application(s) are hereby incorporated by reference.

BACKGROUND OF THE INVENTION

Lipids can become rancid as a result of oxidation. This rancidity caused by oxidation is a major cause of food deterioration. The acceptability of a food product often depends on the extent to which such deterioration has occurred. Moreover, there is increasing evidence of a pathogenic role of endogenous lipid oxidation in a number of chronic and acute disease states. For instance, the association between high-fat diets and chronic diseases such as heart disease are well known. As a result, techniques for assessing the extent of oxidation of foodstuffs have been developed. Sensory analysis, e.g. taste or smell, is one of the most sensitive methods available for detecting lipid oxidation in food which results in rancidity. However, this method has not been practical for routine analysis. As a result, many chemical and physical techniques have been devised in an effort to quantify oxidative deterioration and to correlate the data with, for example, off-flavor development. Chemical methods include those which measure peroxide value, the thiobarbituric test, the Kreis test, those which measure total and volatile carbonyl compounds, and oxirane determination tests. Chromatography based on the physiochemical principles of adsorption, partition, ion exchange, or exclusion, or a combination of these principles, and mass spectroscopy have also been employed. A more complete review of these various methods for measuring the extent of oxidation can be found in Gray (*J Amer. Oil Chem. Soc.* 55:539–546 (1978)). However, many of the existing chemical methods employ high temperature, or strong acid or solution, which classify them as destructive methods and therefore require the commitment of a certain portion of the food as a loss.

Moreover, these conventional methods all suffer from several common disadvantages. For instance, one such disadvantage is that it usually takes an appreciable amount of time to perform most conventional tests on the sample, the length of time being dependent on the complexity of the test. This time delay between when the sample is taken and when the analysis is completed provides a window during which the food's content may have changed, leading to erroneous test results and can be especially troublesome when the time delay is lengthy.

Additionally, situations arise wherein repeated monitoring is desirable, such as, for example, when monitoring daily changes in the freshness of refrigerated meats and the like. Similarly, continuous measurements can be desirable in monitoring the cooking or other preparatory steps in food processing. In such instances, each of the factors of time delay and destruction of the sample (if required for the particular test procedure employed) can be disadvantageous as described above.

In the absence of reliable and rapid measurement techniques, wholesome foodstuffs often must be destroyed because arbitrary shelf-life or refrigeration limitations have expired. Likewise, in the absence of careful attention, foods can be ruined due to overcooking or other errors during processing.

SUMMARY OF THE INVENTION

The present invention relates to a rapid, non-destructive method for analyzing the oxidative status of unsaturated long-chain hydrocarbons, e.g., unsaturated fatty acids in a sample. The method relies on the spectrophotometric detection in a sample of certain chemical groups which have been determined to be reliable as indicators for determining the level of oxidation of unsaturated fatty acids and other unsaturated long-chain hydrocarbons in the sample. In particular, the subject assay can be used to determine, for example, the extent of oxidation of unsaturated fatty acids (including as part of lipids) in whole foods, fats and oils. Thus, the present assay enables the calculation and continued monitoring of the shelf-life of foodstuffs containing lipids and other forms of polyunsaturated fatty acids, such as meats, convenience and snack foods, and cooking oils. Likewise, the degree of oxidation of polyunsaturated fatty acids in a foodstuff can be used to determine the freshness of the sample, which can be indicative of an expected flavor. As described below, the present invention solves such problems in the prior art as time delay and destruction of the sample in that the subject assay can be performed nearly instantaneously and non-destructively.

Accordingly, systems and methods for material analysis are disclosed in which an organic sample (e.g., a foodstuff, tissue sample or petroleum product) is illuminated at a plurality of discrete wavelengths which are absorbed by fatty acid and/or fatty acid oxidation products in the sample. Measurements of the intensity of reflected (or absorbed) light at such wavelengths are taken, and an analysis of reflection ratios for various wavelengths is performed. Changes in the reflection ratios are correlated with the oxidative state of fatty acids present in the material.

In one aspect of the invention, the oxidation state of unsaturated long-chain hydrocarbons in a sample can be detected by (i) irradiating the sample with electromagnetic radiation at a plurality of wavelengths including a reference wavelength and a sample wavelength, wherein absorption of light at the sample wavelength varies with the state of oxidation of hydrocarbons in the sample, and the reference wavelength is sufficiently removed from the sample wavelength so that absorption of light at the reference wavelength is substantially insensitive to the concentration of oxidized hydrocarbons; (ii) detecting radiation absorbed or scattered by the sample at each of the sample and reference wavelengths; (iii) determining the ratio of absorbance, transmittance or reflectance at the sample wavelength and the reference wavelength; and (iv) comparing the ratio to a predetermined value to determine the oxidation state of unsaturated long-chain hydrocarbons in a sample. In preferred embodiments, the sample wavelength is an infrared wavelength, e.g. in the range of 700 nm to 50,000 nm, though more preferably the sample wavelength is in the near infrared, e.g., in the range of 700 nm to 2500 nm. In certain embodiments, the radiation scattered by the sample is detected by Raman spectroscopy.

Other exemplary uses to which the subject assay can be put include diagnostic uses, such as in determining the oxidative stress level of a tissue sample, as, for example, to predict the presence of future risk of tissue ischemia, e.g. myocardial ischemia (artherosclerosis), hepatotoxicity, or tumor growth. The subject assay can also be used to assess the preparation of liposomes and subsequent shelf-life, such as in the preparation of drug and pesticide immoluants.

Moreover, the assay can be used to monitor oxidation of unsaturated hydrocarbons in petroleum products. In preferred embodiments of the invention, detection of the oxidation product of unsaturated fatty acids comprises the use of optical detection means, e.g. infrared or ultraviolet-visible spectrometry, for determining the concentration, or ratio relative to other constituents of the sample, of intermediates of fatty acid oxidation, or chemical features of unoxidized fatty acids which are destroyed upon oxidation, or a combination thereof. Exemplary chemical features which can be use to determine the oxidative state of unsaturated fatty acids include cis-type double bonds, vinyl protons and vinyl hydroperoxyl groups of the fatty acids in the sample.

The present invention also relates to the discovery of a novel intermediate compound in the oxidative degradation of lipids. The intermediate compound has the following general formula:

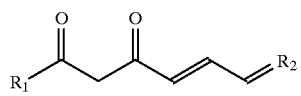

wherein R1 and R2 each independently represent a substituted or unsubstituted $C_1$–$C_{19}$ aliphatic group which can contain one or more heteroatoms, e.g., wherein $R_1$ or $R_2$ or both is terminated by a COOH moiety or one of $R_1$ or $R_2$ is a lipid head group such as a glycerol moiety, a phosphoglycerol, a diacylglycerol, a phosphatidyl group, or a sphingomyelin. By monitoring the presence and concentration of the conjugated diketal intermediate, the degree of oxidation of a lipid sample can be determined.

Therefore, another aspect of the invention features methods of detecting oxidation of polyunsaturated long-chain hydrocarbons, e.g., unsaturated fatty acids, in a sample by detecting the concentration of conjugated diketal hydrocarbons in the sample. The conjugated diketal hydrocarbons can be detected by chromatographic, spectrophotometric, spectrometric or wet chemistry methods in samples such as biological samples, foodstuffs, liposome samples, a petroleum product, or a sample of one or more unsaturated hydrocarbons. Conjugated diketal hydrocarbons can also be detected in a sample using either infrared, near infrared, or ultraviolet-visible electromagnetic radiation and detecting molecular vibrational modes characteristic of a conjugated diketal or detecting molecular electronic modes characteristic of a conjugated diketal, respectively.

BRIEF DESCRIPTION OF THE DRAWINGS

FIG. 1A illustrates a simplified scheme showing products formed from autoxidation of unsaturated lipids.

FIG. 5A illustrates that no significant difference in the intensity of the vinyl methylene protons (18 3000 $cm^{-1}$) occurs upon removing the skin of the fish sample (top spectra -skin on; bottom spectra -skin off). FIG. 5B illustrates that the relative intensity of the vinyl methylene proton signal is dependent on the freshness of the sample.

DETAILED DESCRIPTION OF THE INVENTION

Figure 1B:
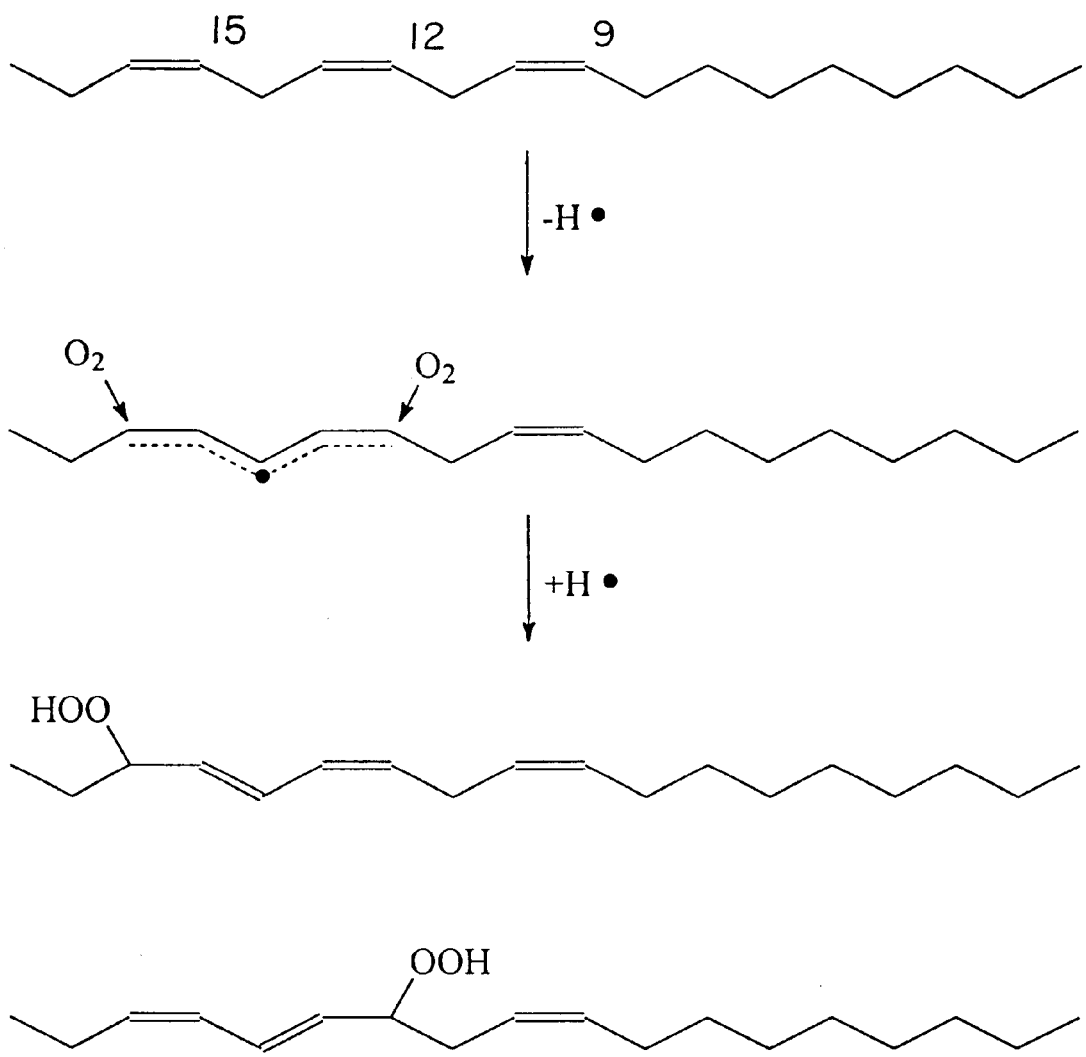
FIG. 1B shows the formation of hydroperoxide intermediates of linolenate.

It is generally accepted that the process of lipid oxidation, particularly in food and tissue, proceeds by way of a free radical mechanism called autoxidation, which can be described in terms of initiation, propagation, and termination processes. However, it will be appreciated by those skilled in the art that term is considered to be a misnomer in that this oxidative process requires a catalyst in biological systems since the triplet state of oxygen forbids direct reaction of molecular oxygen with other biomolecules. Evidence indicates that lipid autoxidation, in foods for example, may be initiated by a number of mechanisms including: (a) singlet oxygen; (b) enzymatic and non-enzymatic generation of partially reduced or free radical oxygen species (i.e., hydrogen peroxide, hydroxyl radical); (c) active oxygen iron complexes; and (d) thermal or iron-mediated homolytic cleavage of hydroperoxides. Generation of hydroperoxides of saturated fatty acids can be formed following exposure to light in the presence of oxygen and a photosensitizer, e.g. riboflavin or cholesterol, which activates the oxygen. Details of these mechanisms can be found in a number of review articles, such as that by Stan Kubow ((1992) *Free Radical Biology and Medicine* 12:63–81) and E. N. Frankel ((1984) *JAOCS* 61:1908–1917. Once the reaction has been initiated via a catalyst, however, the process is autocatalytic in the sense that the oxidation products catalyze the reaction and cause an increase in the reaction rate as oxidation proceeds.

As illustrated by FIG. 1A, unsaturated fatty acids can contain partially activated hydrogen atoms (e.g., those in the methylene bridge separating two double bonds) that are susceptible to removal by free radicals. In molecules susceptible to this process of hydrogen atom abstraction, active oxygen species such as hydroxyl or perhydroxyl radicals (the protonated form of superoxide anion) can induce formation of a new free radical from a target molecule while becoming electrically stabilized themselves. That is, the abstraction of a hydrogen adjacent to a double bond is favored because of the formation of a stable allylic radical in which the electrons are delocalized over three carbon atoms. This process is especially likely to occur in polyunsaturated fatty acid molecules.

In the propagation reaction, the fatty acid radical formed following initiation will react with molecular oxygen to form a peroxyl radical (FIG. 1A). In most systems where oxygen is present, the reaction of the fatty acid radical with oxygen is very fast, and therefore the concentration of the peroxyl radical is much higher than that of the fatty acid radical. The reaction of a peroxyl radical with another polyunsaturated fatty acid yields a fatty acid hydroperoxide and a fatty acid radical, thus conserving the number of free radicals in the reaction sequence. Overall, this reaction has a pyramidal effect in which a relatively few initiating radicals break down many polyunsaturated fatty acids.

Due to resonance stabilization of the fatty acid radical species, the reaction is typically accompanied by a shifting of the double bonds resulting in the formation of a mixture of isomeric hydroperoxides usually containing conjugated diene groups. As shown in FIG. 1B, linoleate oxidation proceeds by hydrogen abstraction from the doubly allylic (bis-allylic) methylene on carbon-14 to produce a delocalized pentadienyl radical. Oxygen attack at the end positions produces a mixture of conjugated 12- and 16-hydroperoxide isomers with the trans,cis-configuration. The analagous reaction, beginning with abstraction of a hydrogen at carbon-11, can occur to yield the conjugated 9- and 13-hydroperoxides (not shown). Experimental evidence indicates that a significant proportion of the conjugated hydroperoxides assume the trans,trans configuration, which increases with the level and temperature of autoxidation.

Lipid oxidation products are often present in unknown amounts in foods which contain polyunsaturated fatty acids. In food, these oxidation reactions lead to the breakdown of lipids and to the formation of a wide array of oxidation products. The nature and proportion of these products can vary widely between foods and depends on the composition of the foods as well as numerous environmental factors. As set out above, the prior art analytic techniques for assessing the extent of oxidation of polyunsaturated fatty acids have traditionally relied on assays which do not present results in a timely manner, which require some destruction of the sample, or both. In constrast, one aspect of the present invention relates to a rapid, non-destructive method for analyzing the oxidative status of unsaturated long-chain hydrocarbons, e.g., unsaturated fatty acids, in a sample. The subject method relies on the spectrophotometric detection of certain chemical features of a polyunsaturated hydrocarbon or an oxidative product thereof which have been ascertained to be reliable as indicators for at least semiquantitatively determining the level of oxidation of unsaturated fatty acids, or other unsaturated long-chain hydrocarbons, in the sample.

As a general overview of the subject method, the oxidation state of unsaturated long-chain hydrocarbons in a sample can be detected by irradiating the sample with electromagnetic radiation at a plurality of wavelengths, including at least one each of a reference wavelength and a sample wavelength. The sample wavelength is chosen to be sensitive to the state of oxidation of hydrocarbons in the sample in that it is quantum matched with an electronic or vibrational modes of a distinct chemical feature of a hydrocarbon, which feature is destroyed upon oxidation, or alternatively, a unique chemical feature of an oxidative product of the hydrocarbon which feature is created during the oxidation process. Exemplary chemical features of the fatty acids in the sample which can be use to determine the oxidative state of unsaturated fatty acids include geometry about double bonds (e.g. cis-type and trans-type), presence of absence of allylic or bis-allylic protons (e.g. protons of vinyl methylene groups), hydroperoxyl groups, enolic protons (e.g. on methylene groups between ketones of conjugated diketal fatty acid intermediates). Other chemical features which can be used, including those which are useful as internal standards, will be apparent from the following description. Conversely, the reference wavelength is picked to be sufficiently removed from the sample wavelength so that absorption of light at the reference wavelength is substantially insensitive to the concentration of oxidized hydrocarbons. The reference wavelength therefore provides an internal standard for calibrating or base-line correcting the measured absorption at the sample wavelength permitting different samples to be compared with one and other.

The radiation absorbed or scattered by a sample at each of the sample and reference wavelengths is detected, and the ratio of absorbance, transmittance or reflectance of radiation at the sample wavelength to radiation at the reference wavelength is calculated. This ratio can subsequently be compared to a predetermined value, e.g. such as obtained from control specimens of similar origin to the sample, in order to determine the oxidation state of unsaturated long-chain hydrocarbons in a sample. Accordingly, model data can be generated for a particular type of food sample, such as a type of fish, poultry, beef, pork, oil, etc., by determining the value for the sample-to-reference ratio for specimens of representative oxidation states, e.g. ranging from fresh to spoiled or rancid. Data obtained from a previously uncharacterized sample can then be compared with the model data for that type of food, and the oxidative state of the unknown sample deduced. The oxidative state can be cast in the model data as, for example, remaining shelf-life of the product, degree of spoilage of the product, and/or expected taste quality of the product.

In particular, the subject assay can be used to determine, for example, the extent of oxidation of unsaturated fatty acids (including as part of lipids) in whole foods, fats and oils. Thus, the present assay permits the calculation and continued monitoring of the shelf-life of foodstuffs containing lipids and other forms of fatty acids, such as meats, convenience and snack foods, and cooking oils. The degree of oxidation of unsaturated fatty acids in a foodstuff can also be used to determine the freshness of the sample, as may be useful in accessing whether the sample is likely to have an expected flavor.

The subject assay can also be used diagnostically, such as for determining the level of oxidative stress of a tissue sample, as, for example, to predict the presence or future risk of tissue ischemia, e.g. myocardial ischemia (artherosclerosis), hepatotoxicity, or tumor growth. The subject assay can also be used to assess the preparation of liposomes and subsequent shelf-life, such as in the preparation of drug and pesticide immoluants. Moreover, the assay can be used to monitor oxidation of unsaturated hydrocarbons in petroleum products.

The detection of oxidative products of unsaturated hydrocarbons, particularly polyunsaturated fatty acids, include ascertaining the level of certain intermediates, such as the conjugated diene, the hydroperoxide, and the conjugated diketal intermediates (described below). It will be understood that such hydrocarbons can be substituted (i.e., the replacement of a methylene proton with, for example, a halogen, a hydroxyl, an alkoxyl, a thiol, a phosphoryl, an amino, or a nitro group) particularly in circumstances wherein the hydrocarbon, e.g. a fatty acid, is used to generate a liposomal preparation. Furthermore, hydrocarbons can contain one or more heteroatoms e.g., sulfur, phosphorous, oxygen, or nitrogen, in place of, or in addition to, one or more carbon atoms. Likewise, the polyunsaturated hydrocarbon, particularly fatty acids, can be terminated by a COOH moiety, a lipid head group such as a glycerol moiety, such as a phosphoglycerol, a diacylglycerol, a phosphatidyl group, a sphingomyelin, or an acylated alkanolamine. Unsaturated hydrocarbons can be dienes or polyenes (i.e., have two or more double bonds) which have double bonds in either the cis or trans formation, and can have one or more triple bonds. Where the hydrocarbon is a fatty acid, it may be a part of a lipid.

As used herein, the term "fatty acid" refers to a long chain (C8 to C26) aliphatic carboxylic acid. A fatty acid molecule has two distinct regions: a long hydrocarbon chain, which is hydrophobic (water insoluble), and not very reactive chemically, and a carboxylic acid group, which can be ionized in solution, extremely hydrophilic (water soluble), and readily forms esters and amides. Unsaturated fatty acids can have one or more double or triple bonds in the carbon chain.

Exemplary fatty acids, whose oxidative products can be detected by the subject assay, include unsaturated forms of myristic acid (C14), palmitic acid (C16), stearic acid (C18), arachidonic acid (C20), behenic acid (C22), lignoceric acid (C24) and cerotic acid (C26). For instance, the polyunsaturated fatty acid can be an oxidation product of such fatty acids as C14:X, C16:X C18:X, C20:X, C22:X, C24:X, or C26:X, wherein X is an integer from 2 to 12 and indicates the number of double bonds in the hydrocarbon backbone. In a representative embodiment, the level of oxidation of fatty acids in a sample can be determined by detecting oxidation intermediates of unsaturated fatty acids such as stillingic acid (11:2), cis-linoleic acid (18:2), $\alpha$-linolenic and $\gamma$-linolenic acids (18:3), c-Parinaric acid (18:4), arachidonic acid (20:4), Timnodonic acid (20:5), omega-6 polyunsaturates, omega-3 polyunsaturates, docosadienoic acid (20:2), adrenic acid (22:4), clupanodonic acid (22:6), teracosatertraenoic acid (24:4), Hexacosapentaenoic acid (26:5), or Octacosapentaenoic acid (28:5). Other exemplary fatty acids are found in, for example, *Practical Manual on Lipid Analysis*, ed. by Alvarez and Touchstone (Norell Press, Mays Landing, N.J.: 1991).

Moreover, it is contemplated by the present invention that such fatty acids could be in the form of lipids. The term "lipid" includes fats or fat-like substances. The term is descriptive rather than a chemical name such as protein or carbohydrate. Lipids include true fats (i.e., esters of fatty acids and glycerol), lipoids (i.e., phospholipids, cerebrosides, waxes) and sterols (i.e., cholesterol, ergostrol). Lipids can be a target of oxidation through mechanisms, such as autoxidation.

In general, the sample to be tested in the subject assay comprises one or more hydrocarbons, e.g., a sample of one or more unsaturated fatty acids, or a liposome sample. The sample can be, to illustrate, a biological sample, a foodstuff, or a petroleum product. Biological samples include blood and tissue. Tissue samples can be analyzed either ex vivo or in vivo.

The term "foodstuff" is intended to include those substances used or capable of being used as food. As such, foodstuffs can include whole foods such as meat and fish, cooking oils, fats and dairy products as well as other foodstuffs that can be subject to lipid oxidation. Petroleum products are derived from petroleum, a highly complex mixture of paraffinic, cycloparaffinic (naphthenic) and aromatic hydrocarbons, containing a low percentage of sulfur and trace amounts of nitrogen and oxygen compounds.

Petroleum products include those obtained by cracking or distillation such as hydrocarbon gases (i.e., ethane, propane, butane), naphtha, gasolme, kerosene, fuel oils, gas oil, lubricating oils, paraffin wax and asphalt. From the hydrocarbon gases, ethylene, propylene and butylene can be obtained. These are important industrial intermediates, being the source of alcohols, ethylene glycols and monomers for a wide range of plastics, elastomers and pharmaceuticals. Petroleum products also include petrolatum, (petroleum jelly), a semisolid or liquid mixture of hydrocarbons derived by distillation of paraffin-base petroleum fractions.

Liposomes include lipid vesicles made up of one or more lipid bilayers containing phospholipids and/or nonphospholipids. "Liposomes" can include vesicles derived from natural lipids, as well as those from synthetic lipids.

A preferred method for detecting the level of fatty acid oxidation in a sample according to the teachings of this invention involves optically detecting intermediates of fatty acid oxidation, or detecting those chemical features of unoxidized fatty acids which are destroyed upon oxidation, or a combination thereof. As should be clear from the discussion below, the language "optically detecting" is intended to include measuring the absorbance and/or transmittance of light by a sample when employing a spectrophotometric means. The spectroscopic means can incorporate the process of optically detecting the absorbance or transmittance of light by a sample.

As used herein "spectrophotometric means" includes a means for spectroscopically analyzing a sample, e.g. a sample of foodstuff or a tissue in a patient using electromagnetic radiation. The means can employ, for example, UV-VIS spectrometry, IR spectrometry or Raman spectrometry. For instance, spectrophotometric means can be used to detect the conversion of cis-type to trans-type double bonds of such fatty acids as C14:X, C16:X C18:X, C20:X, C22:X, C24:X, or C26:X. Similarly, the disappearance of vinyl methylene, or the appearance of a vinyl hydroperoxide can be detected photometrically and used to determine the oxidative state of the fatty acids. In preferred embodiments, the spectrophotometric means permits non-destructive measurements to be made of the sample, though non-destructive is understood to permit insertion of a probe into a sample so long as the integrity of the sample is not appreciably disrupted. Exemplary chemical features for detecting conversion of unsaturated fatty acids by oxidation, including useful features for internal standards, are provided in Table I below. It will be understood that these values represent the optimal wavelength for each of the absorbance peaks of interest, but that these peaks are not infinitely sharp, but rather, due to Boltzman-like distribution of the transition states, are typically Gausian or Lorentzian in shape such that a variation in the detection frequency of up to one half the linewidth can still result in specific detection of the chemical feature of interest. Moreover, it will be appreciated that the optimal wavelength(es) for detection of a particular chemical feature may also vary from one type of sample to the next, as well as from one spectrometer to the next, due to such variables as difference in illumination source power, detector response, electrical noise, optics provided for illuminating the sample, and calibration of equipment. However, each of these factors are well known in the spectrophotometric art and can be controlled for using no more than routine experimentation.

TABLE I

Maximal Absorption Wavelengths for Useful Vibrational Transitions

| Group | Fundamental | 1st Overtone | Combination Band |
|---|---|---|---|
| chain methylene C—H stretch | 3417 (asym) | 1715 | 1400 |
| R—(CH$_2$)$_n$-R' | 3505 (sym) | 1760 | 2300/2500 |
| vinyl methylene C—H stretch (e.g. bis-allylic/allylic) R—CH$_2$—CH=CH—CH$_2$—CH=CH—CH$_2$—R' | 3350 | 1677 | 2115/2175 |
| R—CH=CH—CH$_2$—CH=CH—R' (cis) | | 2138 | |
| R—CH=CH—CH$_2$—CH=CH—R' (trans) | | 2010 | 1677/1180 |
| Hydroperoxide O—H stretch R—CH—ROOH | 2950 | 1450 | |
| R—C=C—R' | 6024 | 3012 | |
| methylene C—H bend R—(CH$_2$)$_n$-R' (bending mode) | 6944 | 3472 | (bending mode) |
| R—C(=O)—R' | 5747 | | | wavelengths are in nm.; asym: asymmetrical stretching; sym: symmetrical stretching In one embodiment of the subject assay, the oxidation of the fatty acid can be quantitated by detecting molecular vibrational modes characteristic of fatty acids or their oxidation intermediates, as for example the conjugated diketal intermediate described herein, or various chemical features distinct for one of either an unoxidized fatty acid or an oxidation intermediate. This aspect of the method comprises irradiating the sample with electromagnetic radiation, e.g., infrared radiation, e.g., preferably near infrared radiation, in a wavelength range which is converted by the sample into molecular vibrations, e.g., in the wavelength range of infrared radiation, and measuring at least one of an absorption or transmission of the electromagnetic radiation by the sample. Infrared radiation refers broadly to that part of the electromagnetic spectrum between the visible and microwave regions. This encompasses the wavelengths from about 700 nm to about 50,000 nM. Near infrared radiation includes wavelengths in the range of about 700–2500 nm. For instance, it has been discovered that fatty acid oxidation levels can be determined by measuring near infrared absorption at particular wavelengths. As used herein, the term "near infrared" or "near IR" is intended to encompass light in a spectrum ranging from about 700 to about 2500 nm, more preferably from about 1300 to about 2400, and, in some instances, most preferably from about 14000 to about 2200 nm.

Although the infrared spectrum is characteristic of the entire molecule, certain groups of atoms give rise to bands at or near the same frequency regardless of the structure of the rest of the molecule. It is the persistence of these characteristic bands that permits the practitioner to obtain useful structural information by simple inspection and reference to generalized charts of characteristic group frequencies. In the subject assay, the conjugated diketone is a structure that is likely to be persistent irrespective of the length of the hydrocarbon chain. Furthermore, as described herein, other chemical structures of the fatty acids, or oxidative products thereof, have been determined that are suitable for detection by infrared means and which provide useful information for determining the oxidative state of a sample, such as groups associated with the vinyl carbons of unsaturated fatty acid (either oxidized or unoxidized), or stereochemical features associated with double bonds in oxidized and unoxidized fatty acids. As provided in Table I above, three exemplary infrared wavelengths for detecting fatty acid oxidation include peaks centered about 2138 nm (for cis double bond of fatty acid), 3350 nm, 1677 nm, 2115 nm, or 2175 nm (for C-H stretching of the protons on the vinyl methylene, e.g. the bis-allylic protons), and 1450 nm (O-H stretching of a hydroperoxide).

Infrared radiation of frequencies less than about 100cm$^{-1}$ (wavelengths longer than 10,000 nm) can be absorbed and converted by a fatty acid molecules into energy of molecular rotation. This absorption is quantitized; thus a molecular rotation spectrum can consist of discrete lines. Infrared radiation in the range from about 10,000–100 cm$^{-1}$ (1000 nm–10,000 nm) can be absorbed and converted by a fatty acid molecule into energy of molecular vibration. This absorption is also quantitized, but vibrational spectra appear as bands rather than as lines because a single vibrational energy change can be accompanied by a number of rotational energy changes. The frequency or wavelength of absorption depends on the relative masses of the atoms, the force constants of the bonds and the geometry of the atoms in the fatty acid.

Band positions in infrared spectra are presented either as wavenumbers or wavelengths and are understood to be equivalent. The wavenumber unit (cm$^{-1}$, reciprocal centimeters) is used most often since it is proportional to the energy of the vibration and since most modern instruments are linear in the cm$^{-1}$ scale. Wavelength, $\lambda$ is referred to herein in terms of micrometers ($\mu$m, 10$^{-6}$ meters) or nanometers (nm, 10$^{-9}$ meters). Wavenumbers are reciprocally related to wavelength as follows:

$$cm^{-1} = \frac{1}{\mu m} \times 10^{-4}.$$

Wavenumbers are often called "frequencies"; this is not rigorously correct, since wavenumbers are 1/$\lambda$ and frequency (v) is c/$\lambda$. Such "frequency" for wavenumber terminology is quite common and is probably not a serious error if the missing speed-of-light term (c) is remembered.

Band intensities can be classically expressed either as transmittance (T) or absorbance (A), though for the purpose of this application both of will be understood as within the meaning of the term "absorbance" or "absorption". As used in the art, transmittance is the ratio of the radiant power absorbed by a sample to the radiant power incident on the sample, and absorbance is the logarithm, to the base 10, of the reciprocal of the transmittance (A=log$_{10}$(1/T)). The term absorbance or absorption further include scattered light, such as measured in Raman spectroscopy.

Moreover, other forms of vibrational spectroscopy, such as Raman spectroscopy, can be used as part of the subject technique for characterizing fatty acid oxidation intermediates. The Raman vibrational spectrum of these molecules can consist of a series of sharp lines which constitute a unique fingerprint of the specific molecular structure, and can be distinguished from the unoxidized form of the hydrocarbon as well as other intermediates. There are various instances where it would be desirable to measure the vibrational spectrum of a sample in a remote or hostile environment, such as in vivo measurement of oxidative stress to a tissue. To measure spectroscopic absorption over optical fibers, light from a source is delivered to the sample over one fiber and the light after passage through the sample is collected by another fiber. The collected light is directed back to an instrument for analyzing its wavelength and/or intensity, such as a monochrometer and a photodetector. However, silica or plastic optical fibers themselves absorb in the 2 to 50 $\mu$m wavelength region, and so cannot be used for remote measurements of absorption in the infrared spectral region where molecular vibrational transitions occur.

Raman spectroscopy presents a means of obtaining vibrational spectra over optical fibers with visible or near infrared light, and provides a viable alternative to infrared spectrophotometry for use in the subject method. These wavelength regions are efficiently transferred without significant absorption losses over conventional optical fiber materials. In Raman spectroscopy, monochromatic light is directed onto a sample and the spectrum of the scattered light is determined. However, due to a very weak signal, the excitation light must be quite intense, though laser irradiation sources are readily available. In addition, optical filtering is necessary to separate the weak scattered signal from the intense Rayleigh line.

In yet another embodiment of the subject assay, the oxidized hydrocarbons are detected in the sample by detecting molecular electronic modes characteristic of such groups. This aspect of the method includes irradiating the sample with electromagnetic radiation, e.g., ultraviolet-visible radiation, e.g., ultraviolet radiation, in a wavelength range converted by the fatty acid molecules into electronic vibrations/electron orbital transitions, e.g., in the wavelength range of 200–400 nm, e.g., at a wavelength of 275 nm and measuring the absorption of the electromagnetic radiation by the sample. In the ultraviolet and visible region of the spectrum, molecular absorption is dependent on the electronic structure of the molecule. Absorption of energy is quantized, resulting in the elevation of electrons from the ground state to higher energy orbitals in an excited state. For many electronic structures, the absorption does not occur in the readily available portion of the ultraviolet region.

There is, however, an advantage to the selectivity of ultraviolet absorption: characteristic groups can be recognized in molecules of widely varying complexities. As a large portion of a relatively complex molecule can be transparent in the ultraviolet region, a spectrum can be obtained similar to that of a much simpler molecule.

Wavelengths in the ultraviolet region of the spectrum are usually expressed in nanometers or angstroms (Å). The near ultraviolet (quartz) region includes wavelengths of 200–380 nm. The atmosphere is transparent in this region and quartz optics may be used to scan from 200 to 380 nm. Atmospheric absorption starts near 200 nm and extends into the shorter-wavelength region (10–200 nm), which is accessible through vacuum ultraviolet spectrometry.

The total energy of a molecule is the sum of its electronic energy, its vibrational energy, and its rotational energy. Energy absorbed in the ultraviolet region produces changes in the electronic energy of the molecule. These transitions consist of the excitation of an electron from an occupied orbital (usually a non-binding p or binding $\pi$-orbital) to the next higher energy orbital (an antibonding, $\pi^*$ or $\sigma^*$, orbital). The antibonding orbital is designated by an asterisk.

Since ultraviolet energy is quantized, the absorption spectrum arising from a single electronic transition should consist of a single, discrete line. A discrete line is not obtained since electronic absorption is superimposed on rotational and vibrational sublevels. The spectra of simple molecules in the gaseous state consist of narrow absorption peaks, each representing a transition from a particular combination of vibrational and rotational levels in the electronic ground state to a corresponding combination in the excited state. At ordinary temperatures, most of the molecules in the electronic ground state will be in the zero vibrational level; consequently, there are many electronic transitions from that level. In molecules containing more atoms, the multiplicity of vibrational sublevels and the closeness of their spacing cause the discrete bands to coalesce, and broad absorption bands or "band envelopes" are obtained.

The principal characteristics of an absorption band are its position and intensity. The position of absorption corresponds to the wavelength of radiation whose energy is equal to that required for an electronic transition. The intensity of absorption is largely dependent on two factors: the probability of interaction between the radiation energy and the electronic system and the difference between the ground and the excited state. The probability of transition is proportional to the square of the transition moment. The transition moment, or dipole moment of transition, is proportional to the change in the electronic charge distribution occurring during excitation. Intense absorption occurs when a transition is accompanied by a large change in the transition moment. Absorption with $\epsilon_{max}$ values$>10^4$ is high-intensity absorption; low-intensity absorption corresponds to $\epsilon_{max}$ values$<10^3$.

Accordingly, the subject method relies on optically detecting discrete chemical groups of fatty acids which have been determined to be reliable as indicators for at least semiquantitatively determining the level of oxidation of fatty acids in the sample. In general, the method comprises illuminating (e.g. irradiating) the sample at a plurality of discrete wavelengths, e.g. selected from the infrared, visible or ultraviolet spectrum, which correspond to at least one sample wavelength and one reference wavelength. The sample wavelength is defined as being a wavelength for detecting a chemical feature whose existence is dependent on the oxidative state of polyunsaturated hydrocarbons in the sample. The reference wavelength, on the other hand, is selected as a frequency which is not absorbed by the sample in a manner dependent on the oxidation of the polyunsaturated hydrocarbons in the sample. Measurements of the intensity of transmitted, absorbed, or reflected light at such wavelengths are taken, and an analysis of transmittance, absorbance, or reflectance ratios for various wavelengths is performed.

In preferred embodiments, the reference wavelength is closely spaced and can be chosen so as to provide a "baseline" for determining the intensity of the peak of interest, such as the band intensity of a peak arising due to, for example, a cis double bond, a vinyl methylene proton, or a hydroperoxide moiety. Changes in the ratios can be correlated from the sample wavelength (e.g. from the oxidized intermediate) which obviously will vary with the state of oxidation of the sample, and the a second (reference) wavelength, which is sufficiently removed from the sample wavelength so that measurements of light absorption at this second wavelength is relatively insensitive to the concentration of the analyte, and yet which is sufficiently close to the first wavelength to minimize interference from scattering effects and the like. Typically, the window bracketing these closely spaced wavelengths will be less than about 300 nm and preferably less than about 60 nm wide and, in some instances, more preferably less than about 30 nm wide. The reference wavelength can be chosen so as to detect a chemical feature which remains relatively unchanged (e.g. does not change in significant manner) upon oxidation, or can be selected as a wavelength which does not correspond to any sharp absorption bands but which provides baseline correction to compensate for convoluted or "rolling" baselines. Examples of the former are provided below, while an example of the latter is a reference wavelength which is offset from the sample wavelength by 2 to 6 times the linewidth of the absorption/transmission peak due to the specific chemical feature detected at the sample wavelength.

Figure 4A:
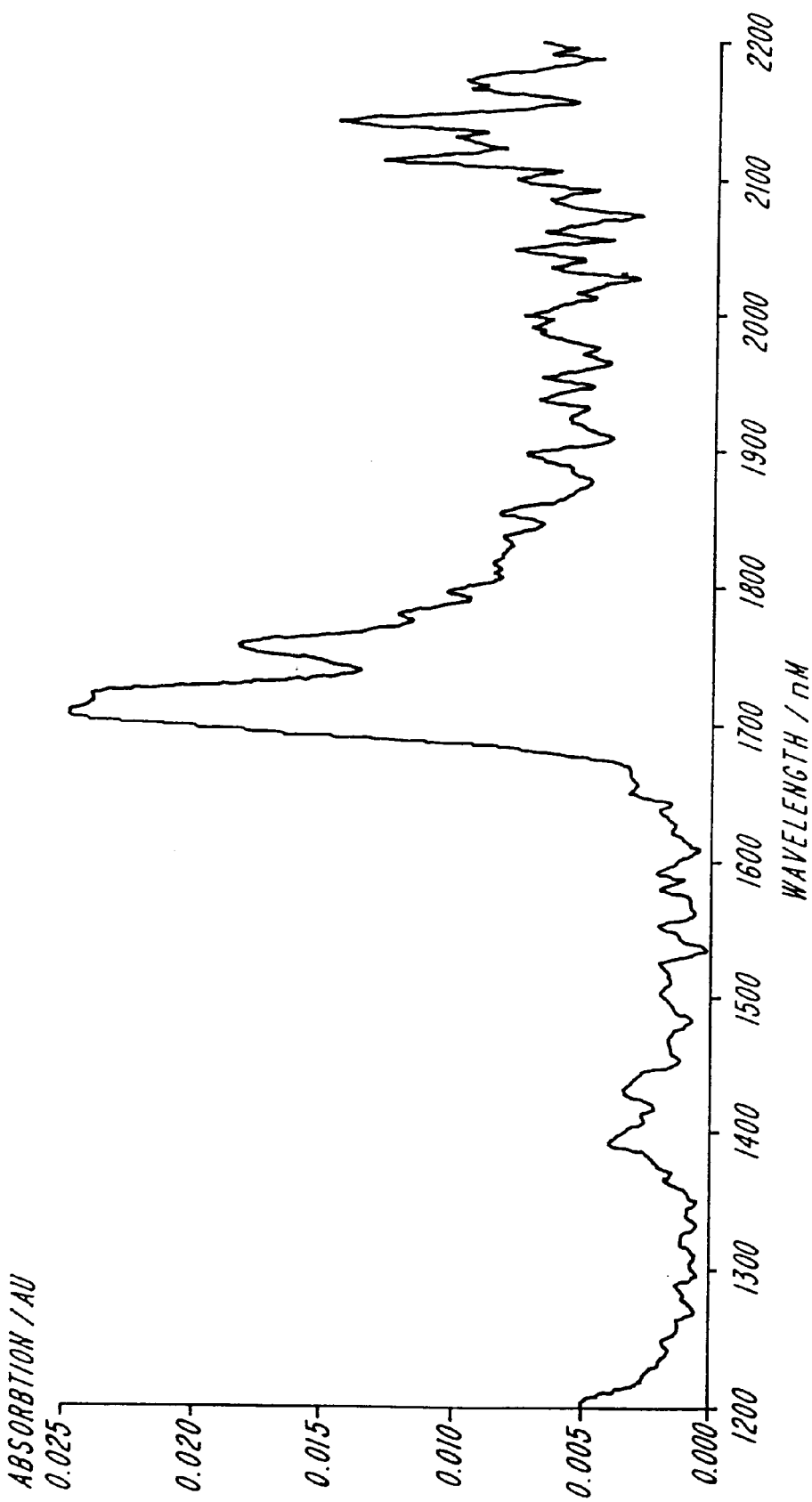
FIGS. 4A, 4B and 4C are near infrared spectra of samples of salmon meat, ranging in freshness from most fresh (FIG. 4A) to less fresh (FIG. 4C).
Figure 4B:
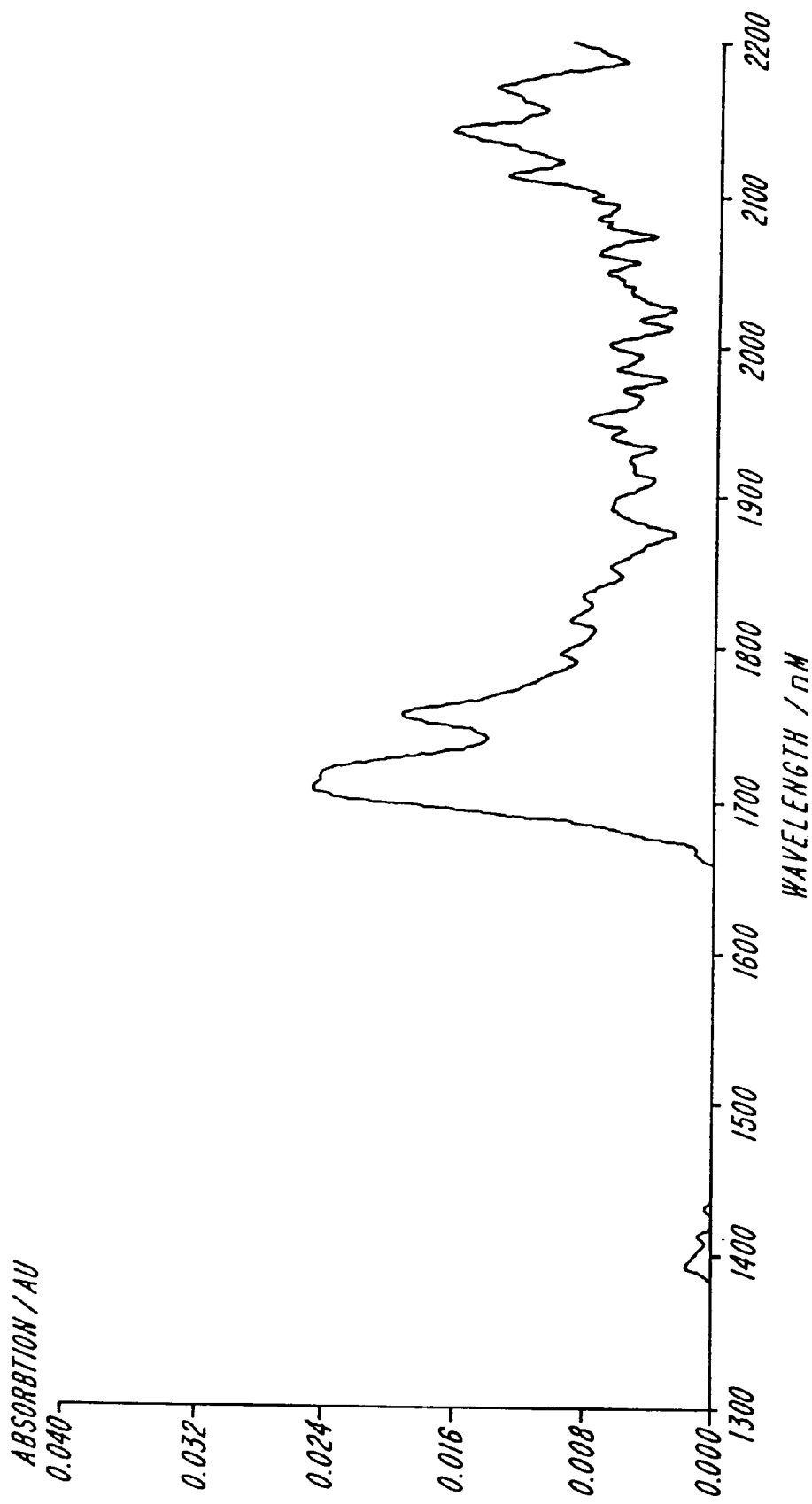
Figure 4C:
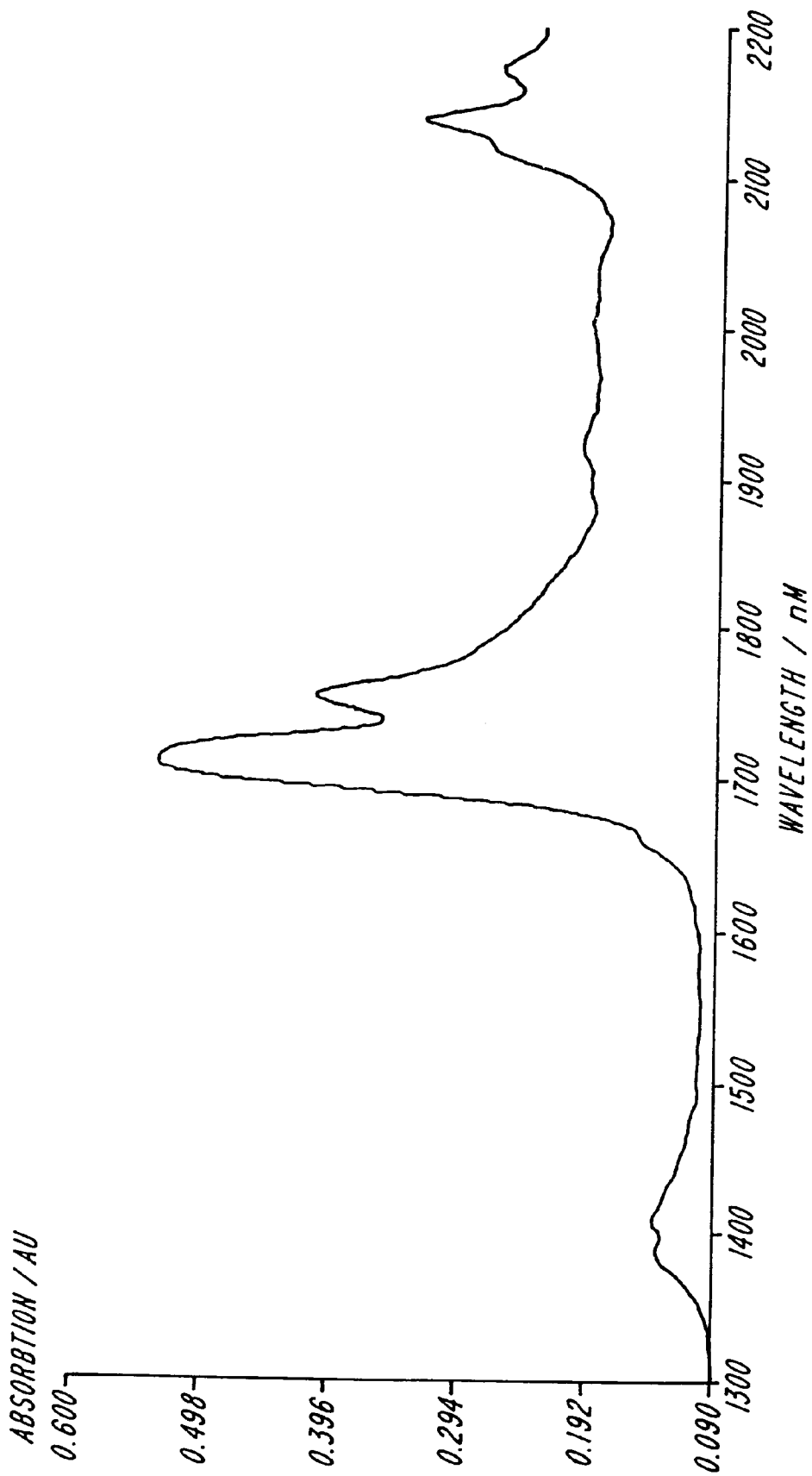

In a representative embodiment, the subject method relies on detecting the loss of bis-allylic and allylic protons from a fatty acid upon formation of oxidization intermediates. For instance, as illustrated in FIGS. 4A–C, a peak at 2115 nm in the infrared spectra of a fish sample corresponds to the presence of the allylic and doubly allylic protons. In the fresh salmon sample (FIG. 4A), the peak is present and, relative to the oxidized samples, is most intense. However, during oxidation, the double bond shifts to yield conjugated dienes and hydroperoxides which result in loss of allylic protons. As is apparent from the spectra of FIG. 4B and 4C, the 2115 nm peak is diminished over time as oxidation of the sample occurs. Therefore, the ratio of absorbance of radiation at wavelength quantum matched with the allylic proton, to absorbance at a reference wavelength (e.g. a wavelength insensitive to the concentration of fatty acid oxidants) can be used to correlate the freshness of the sample. For instance, the ratio of absorbance at the sample wavelength, such as the 2115 nm peak, to the intensity of absorbance at the reference wavelength, such as the 2138 nm peak (1st overtone of cis configuration) or the 1715 nm peak (1st overtone of chain methylene C-H stretch), can be used to determine the oxidative state of the sample.

In similar fashion, the C-H stretching of the protons on the vinyl methylene (e.g. the bis-allylic) can be detected at 3350 nm, and decreases in intensity as oxidation of the fatty acid progresses. An exemplary reference wavelength is 3417 nm, which corresponds the asymmetrical stretching of other methylenes (—$CH_2$—) in the sample and is relatively insensitive to the oxidation.

Figure 5A:
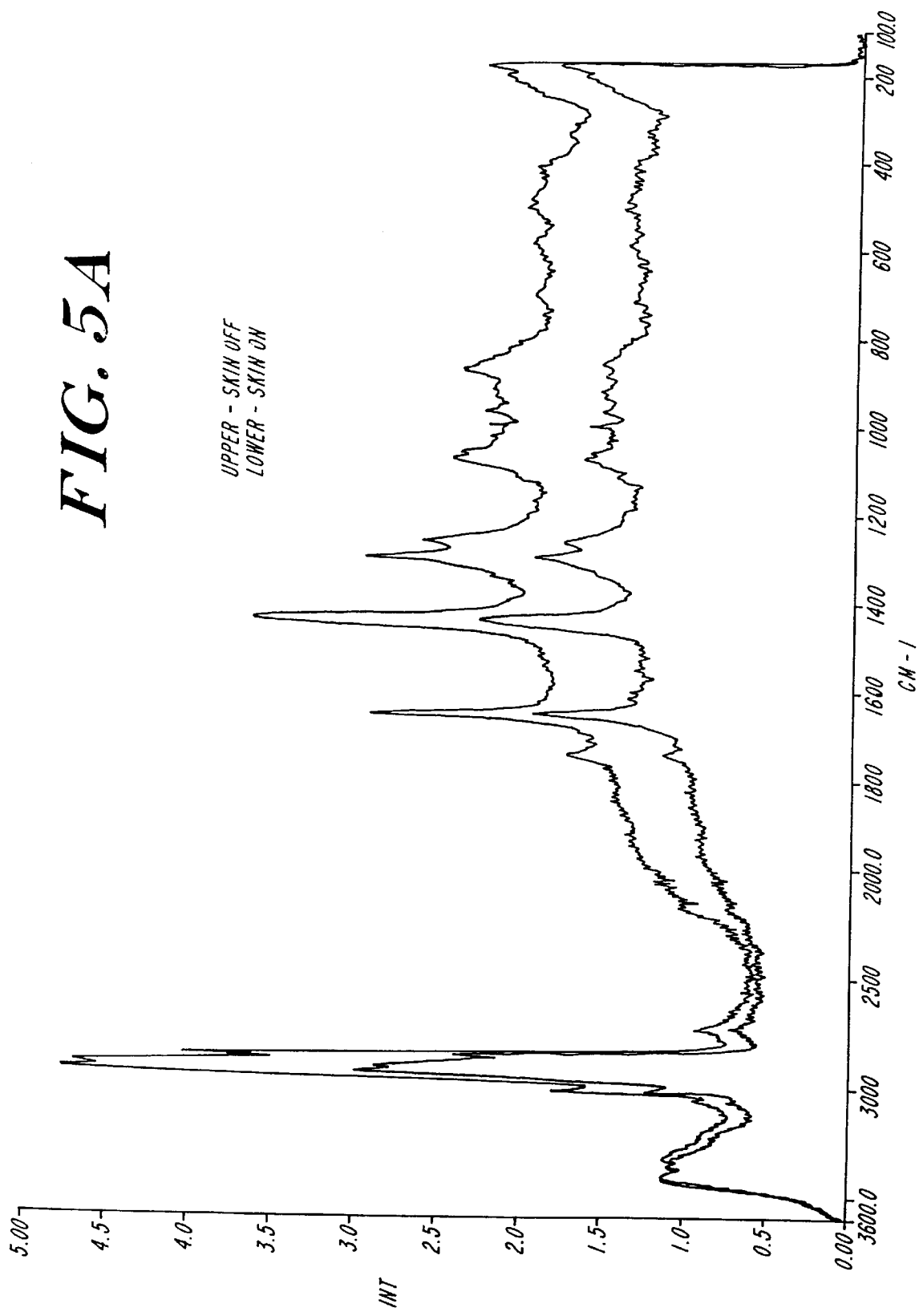
FIGS. 5A and 5B are Raman spectra of samples of salmon meat.

In yet another embodiment, the sample wavelength detects C-H stretching of bisallylic protons present on the vinyl methylene of a fatty acid in the sample, e.g. H-(H)C-C=C, by Raman spectroscopy. For example, FIGS. 5A and 51B illustrate that the vinyl methylene proton is detectable at 3000 $cm^{-1}$ by Raman spectroscopy. As oxidation progresses, the C-H signal will decreases as vinyl methylenes are lost from the sample due to conversion to oxidative products. A convenient reference wavelength is 1450 $cm^{-1}$, which corresponds to a vibrational mode of the C=C bond.

In still another embodiment, the sample wavelength detects an 0-H stretching of an O-O-H group, e.g. of the vinyl hydroperoxide. An exemplary wavelength for detecting this moiety is 1450 nm (e.g., the combination band for this group), with peak intensity increases proportional to oxidation of the sample. As above, the C-H stretch of fatty acids methylenes can be used as an internal standard. In a preferred embodiment, the reference wavelength is the combination band for the methylene C-H stretch at 1400 nm.

Moreover, it should be noted that, in addition to the fundamental transitions, it can be advantageous under certain circumstances to use the overtone and combination bands of these transitions (e.g. as described above). Generally, asymmetric bonds having dipole moments create detectable and distinguishable features in the near infrared region. In particular, combinations and overtones associated with the fundamental infrared absorbance associated with the C-H bonds give particularly intense features. For instance, three overtone bands of the H-C stretching mode and three combination bands of C-H stretching and bending modes are found in the near infrared region. In an exemplary embodiment, the bis-allylic proton, which has a fundamental band at 3350 nm, can also be detected at 1655 nm, 2115 nm and 21175, using its first overtone and combination bands respectively (see Table I). Each set of overtone and combination bands contain similar information. Generally, any overtone band, combination band or combination of overtone and combination bands can be utilized, however, a particular range is generally preferred depending on the system under analysis. A notable benefit to using overtone bands to detect the oxidation intermediates is in the elimination of water bands and other interference bands that are potential problems for detection. The choice of overtone and combination bands for detection will depend largely on the sample to be analyzed, and in light of the present disclosure, can be readily determined by the skilled artisan upon routine analysis with specimens of the sample to be tested.

Moreover, the subject method can include a further step of oxidatively stressing the sample by applying, for instance, thermal or electromagnetic radiation, or a chemical agent which generates free radicals in the sample. Providing an additional step of stressing the sample can be used, for example, to determine the expected storage life (e.g. the shelf life remainder) for the sample being tested. For instance, a control data set can be generated by determining the oxidative response of specimen samples which have ascertainable shelf-lives, e.g. by ascertaining the oxidative state of samples before and after application of the stress. The same determinations can then be carried out on an unknown sample of the same or similar food and, based on comparison with the control data, can be used to calculate the shelf-life remainder for an unknown sample. For instance, the ratio of oxidized fatty acids can be determined for a sample of cooking oil before and after an oxidative stress is applied to the sample, the ratio compared to a data derived from cooking oil samples with known shelf-lifes, and remaining shelf-life from the unknown sample determined accordingly.

Thermal radiation includes heat emitted by a body that is transmitted through an intervening medium or space and absorbed by he sample. Electromagnetic radiation includes energy in the form of electromagnetic waves (e.g., radiant energy or light). Numerous chemical agents are also available which can generate free radicals and therefore be useful in oxidatively stressing the sample. Chemical agents include compounds, metal complexes, and enzymes. For example, hydrogen peroxide can be used to radicalize oxygen in a sample. Enzymes such as lipoxygenase, prostaglandin synthase, NADH dehydrogenase and microsomal oxidase can also generate hydroxyl radicals and/or singlet oxygen through their activities.

In preferred embodiments, the invention provides a non-invasive method for ascertaining the freshness or spoilage of a foodstuff by measuring the oxidation level of unsaturated fatty acids in the foodstuff, such as by optically detecting chemical groups from fatty acid molecules and determining from the absorbtion of optical energy by those groups the levels of fatty acid oxidation, e.g. detecting discrete chemical groups of fatty acids which are unique to fatty acids or certain fatty oxidation products. Such information can be used, in one embodiment, to calculate the shelf-life of a product. However, it will be apparent that this information is also valuable in quality control testing for expected taste, e.g. by detecting oxidation which might alter the taste of the food, such as by spoilage.

Standard samples can be prepared using no more than routine experimentation by, for example, taking a known fresh foodstuff of similar or identical type or size and spectroscophotometrically measuring the level of discrete chemical groups of fatty acids present at different time points and/or before and/or after applying an oxidative stress. The amount of apparent oxidation of the sample can be compared to a standard to determine the freshness of the foodstuff, e.g. by comparing the amount of conjugated diketal fatty acids or measuring the ratio of vinyl methylene protons to methylene protons in the sample. The type of foodstuff will govern how much oxidized fatty acids can be tolerated prior to the foodstuff being considered spoiled.

Cooking oils and fats are often used repeatedly without replacing the oil or fat in restaurants and movie theaters. They are also frequently stored for long periods of time before and during use. During their use, constant heating and cooling of the oil or fat can lead to lipid oxidation and subsequent spoilage causing a health hazard. Accordingly, the invention is also directed to a method of determining the storage or frying half-life of unsaturated lipids in whole foods, fats or oils including optically detecting by spectroscopic means the amount of oxidized fatty acids in the sample, and ascertaining the existing oxidation level of the sample by comparing measured parameters with one or more standard samples of known freshness.

The oxidative stress level of tissue of a subject can indicate the likelihood of subject developing certain disease states. Accordingly, the invention also provides a method of determining the oxidative stress level of a tissue sample including optically detecting by spectroscopic means the level of oxidation of fatty acids which has occurred in a tissue of a subject; and ascertaining the level of oxidative stress of the tissue sample by comparing the that level one or more standard samples of known oxidative stress levels. The term subject is intended to include living organisms, e.g., mammals. Examples of subjects include humans, dogs, cats, mice, rats, and transgenic species thereof.

The term "tissue sample" is intended to include a sample of a group or collection of similar cells and their intercellular substance that act together in the performance of a particular function. The primary tissues include epithelial, connective, skeletal, muscular, glandular and nervous. Tissue samples include samples of myocardial tissue, cerebral-spinal tissue, and hepatic tissue.

As above, the invention subject method can include the further step of oxidatively stressing the tissue sample and comparing the level of oxidized fatty acids before and after the oxidative stress is applied. Where the tissue is myocardial tissue, the level of oxidative stress can be predictive of myocardial ischemia. The oxidative stress level can also be predictive of artherosclerosis or the risk of artherosclerosis. Where the tissue is cerebralspinal tissue, the level of oxidative stress can be predictive of brain ischemia. The oxidative stress level of hepatic tissue can be predictive of hepatotoxicity or the risk of hepatotoxicity. In a tissue comprising hyperplastic or neoplastic cells, the oxidative stress level can be predictive of the presence of tumor cells.

Antioxidants can be effective in preventing or retarding the oxidation of lipids, e.g., via termination reactions. For example, the reactivity of phenolic antioxidants such as α-ctocopherol allows it to intervene to regenerate the original diene and a phenoxyl radical. The antioxidant free radicals are generally too unreactive to propagate the autoxidation.

Accordingly, the invention provides a method for determining the relative effectiveness of a candidate antioxidant in protecting an unsaturated fatty acid from peroxidation including optically detecting, by spectroscopic means, the amount of oxidized fatty acids in a sample of the unsaturated fatty acid over a period of time, in the presence of a candidate antioxidant and comparing a change in the level of oxidation of the fatty acids over time as measured with a change in the level of oxidation over the same time in a similar fatty acid sample lacking the candidate antioxidant.

The invention further provides an apparatus for the non-destructive analysis of the oxidative status of unsaturated lipids in whole foods, fats or oils including optical emission means for irradiating a food sample with optical energy; optical detection means for detecting optical energy which is not absorbed by the food sample in the first and second wavelength ranges, and comparator means for determining the ratio of optical energy transmitted or reflected by the sample in each of the first and second wavelength ranges, wherein the ratio of optical energy transmitted or reflected in each of the first and second wavelength ranges is indicative of the level of oxidation of fatty acids in a sample of the unsaturated fatty acid. In preferred embodiments, the detection apparatus is hand-held.

The subject detection system can be created, for example, by modification of existing spectrophotometers, such as to provide optics appropriate for use with a particular sample (e.g. for contacting meat, submersion in oil, insertion into a body, etc.) and illumination sources for providing optical energy at a desired set of wavelengths (e.g. to detect representative functional groups of fatty acid or fatty acid oxidation intermediates). For example, the laser-based reflectance ratio detector of U.S. Pat. No. 5,239,180 can be adapted for detecting oxidation of fatty acids by providing for illumination and detection at wavelengths corresponding to functional groups of fatty acid or fatty acid oxidation intermediates. Similarly, the devices described in U.S. Pat. Nos. 5,246,004, 5,239,180, 5,222,495, 5,054,487, 5,036,853, 5,028,787, 5,319,200, 4,802,761, 4,975,581, 5,321,265, 5,319,437, 4,550,381 and 5,161,531 can be modified for use in the present invention.

Figure 3A:
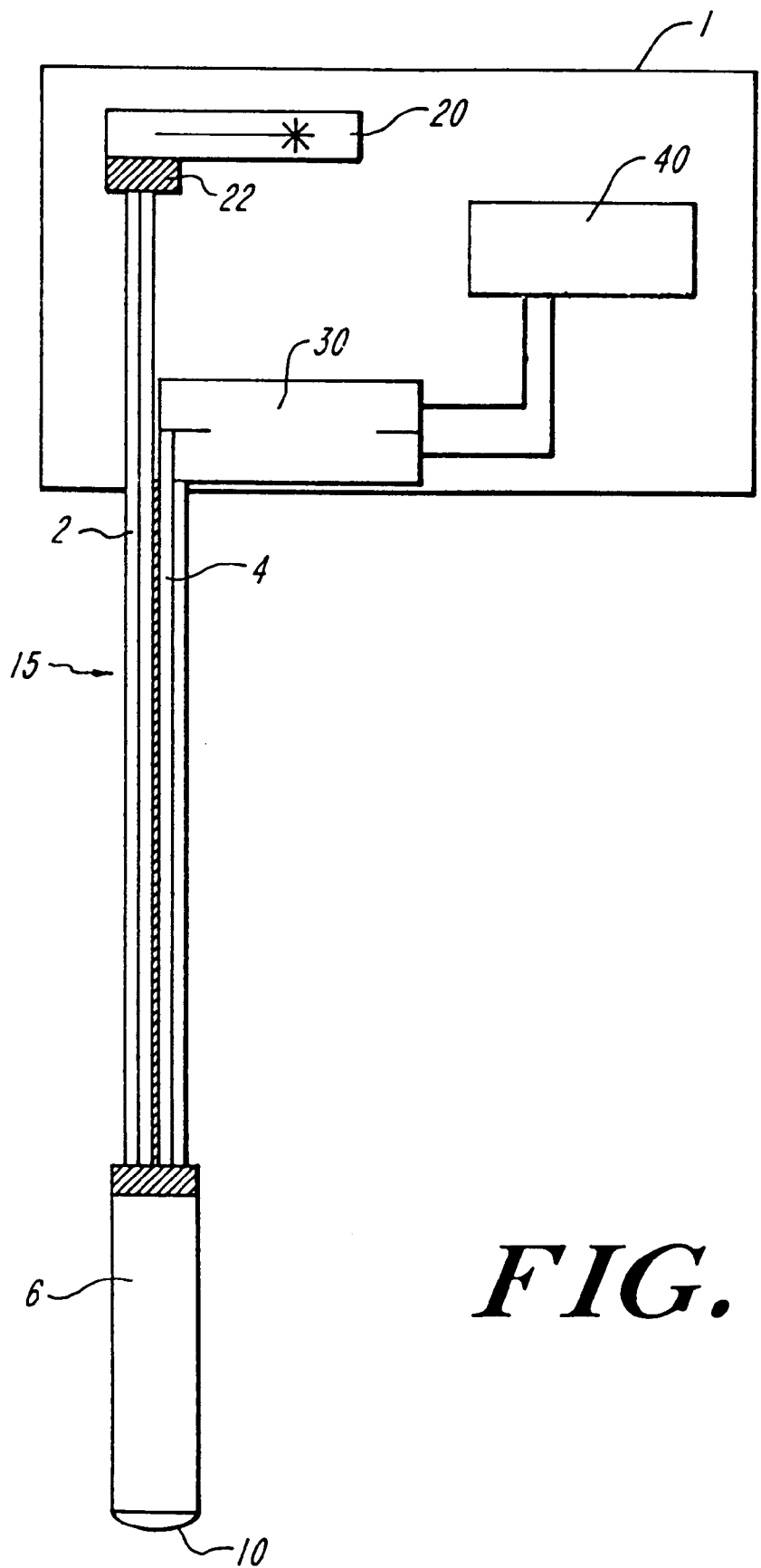
FIG. 3A is an apparatus for the non-destructive analysis of the oxidative status of unsaturated lipids.

In a representative embodiment (FIG. 3A), a system (1) is provided with a fiber optic probe for delivery of two or more distinct wavelengths of light to a sample, preferably a food sample, though it should be clear that the number of interrogation wavelengths, the size and shape of the sampling probe head and the means for transmitting the light to and from the sample can be varied to meet particular needs and applications. For instance, the apparatus can include a single or multiple wavelength illumination source (20), a wavelength specific detector array (30), a reflection comparator means (40), and a power source (not shown).

The illumination source (20) illuminates the material sample at a plurality of wavelengths via the fiber optic bundle (15). In a preferred embodiment, the system is set up to detect near infrared absorption by oxidative intermediates of fatty acids. In such an embodiment, the system comprises a multiple wavelength illumination source, e.g. laser diodes, which provide light at a series of material analysis wavelengths (e.g. from about 500 nm to about 2000 nm).

Moreover, although lasers are described as preferred light sources, other illumination means including a non-coherent, discrete wavelength light sources can be employed, e.g. one possible light source is a tungsten-halogen bulb in a quartz envelope to provide light in the IR wavelength range. In the illustrated embodiment, the diode elements of the illuminator (20) each transmit a predetermined wavelength of light via corresponding optical fiber elements (2) to the probe head (6). Moreover, in circumstances wherein significant fluorescence may occur upon irradiation of a sample, it may be desirable to place a filter in the path of the emitted light or reflected light. For instance, a narrow band filter (not shown) can be used, e.g. one which has a bandwidth of less than about 30 nm and preferably less than about 10 nm and is designed to pass light at a desired.

The use of optical fibers and optical fiber strands has undergone rapid development, particularly within the last decade, and are generally available through commercial sources. See, for example, A. D. Pearson et al. in "Fiber Optics" in the Kirk-Othmer:Encyclopedia of Chemical Technology, 3rd Ed., Vol. 10, John Wiley & Sons, New York, N.Y., pp. 125–147, published in 1980. Also see A. C. Levy, "Optical Fibers," in the Encyclopedia of Polymer Science and Engineering, H. F. Mark et al (ed.) Vol. 7, pp. 1 to 15, John Wiley and Sons, New York, New York, published in 1986. An optical fiber is a clad plastic or glass tube wherein the cladding is of a lower index of refraction than the core of the tube. When a plurality of such tubes are combined, a fiber optic bundle is produced. Optical fibers are flexible and are therefore capable of guiding light in a curved path defined by the placement of the fiber. When light energy is projected into one end of the fiber strand (conventionally termed the "proximal end"), the angles at which the various light energy rays strike the surface are greater than the critical angle; and such rays are "piped" through the strand's length by successive internal reflections and eventually emerge from the opposite end of the strand (conventionally termed the "distal end").

In accordance with the invention, an optical fiber, or fibers, which can carry laser radiation is mounted in a flexible inert plastic catheter material with a transparent protective optical shield over the distal end (e.g. the "probe head"). This probe head is inserted into a sample, e.g. a food sample, and is brought into contact with the portion of the sample from which readings are desired.

The fiber optic bundle (15) is made up basically of a bundle of optical fibers. In the illustrated embodiment, the afferent and efferent optical signals are carried by separate optical fibers, (4) and (2) respectively, within the bundle (15). The diameter of the bundle is preferably about ½ to 10 nm. The fibers within the bundle are preferably randomly arranged to reduce any geometrical collection effects. At the distal end of the fiber optic bundle, the optics terminate in fiber optic probe (6), which may also include a shield lens (10) at the distal probe end so that non-contact probing may be achieved, facilitating examination of areas within a food or tissue sample. Light from source (20) is fed into an input leg (22) of efferent fibers (2) of optic fiber bundle (15). The light entering the fiber optic bundle emerges at the distal end of the fiber, e.g. at probe head (6), and is conducted out of the probe head through probe head shield (10).

The shield (10) may be in the form of a glass, fused silica, sapphire or other transparent member. The shield may be flat, spherical or lens shaped. The periphery of the shield is bonded to the end of the probe wall.

The enclosed protected region provided by the shield can be used to mount or incorporate elements of various kinds. Several fibers can be precisely positioned at different locations within the probe head. Lenses or mirrors, and mechanical or optical aiming and focusing devices can be mounted inside of the probe head. As illustrated, light can be delivered to the tissue via one fiber, and the reflected light returned by means of the same or another "sensing" fiber for spectroscopic or other forms of analysis. The fibers may be secured to each other with an adhesive substance, and likewise may be bonded to the optical shield.

Figure 3B:
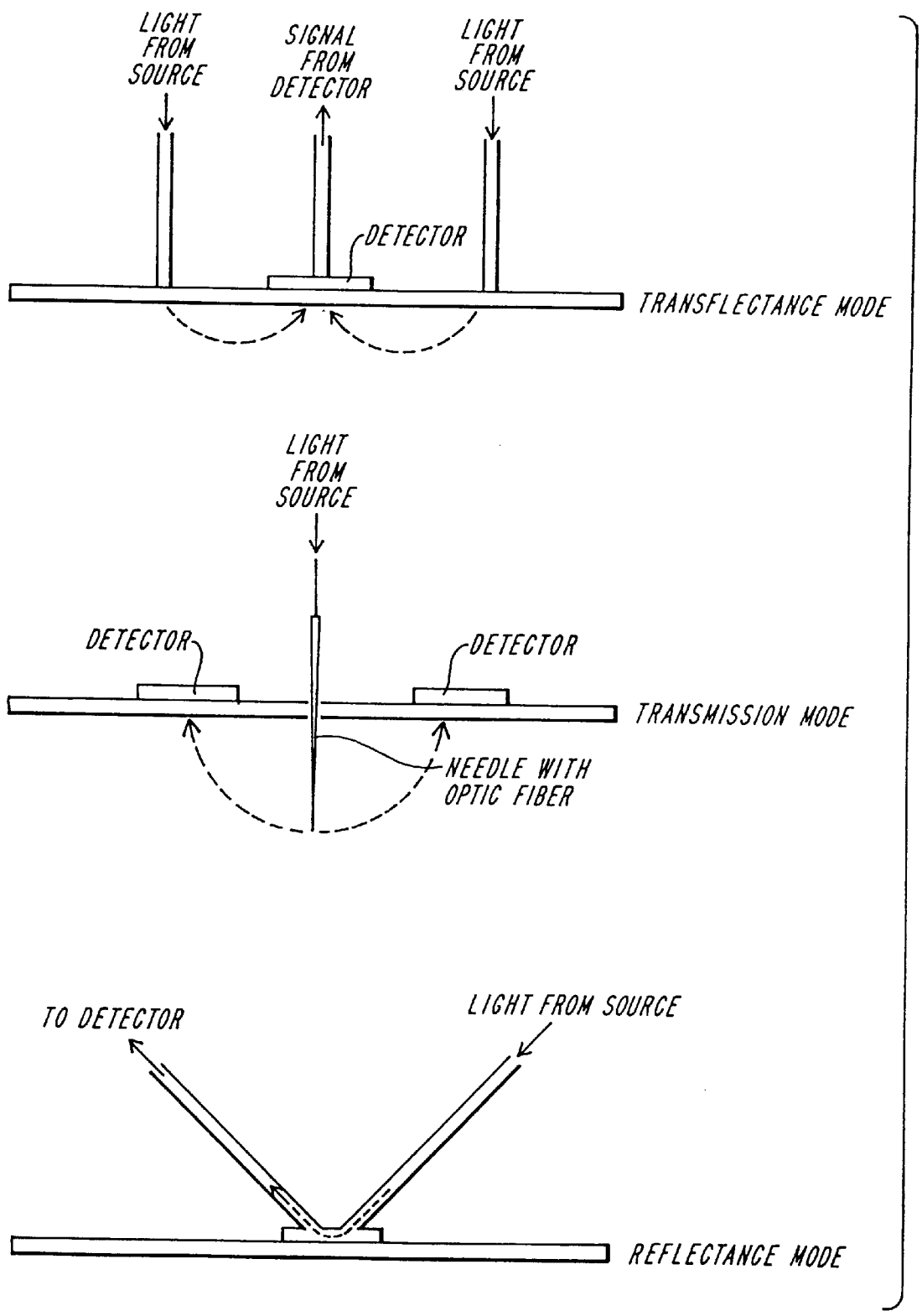
FIG. 3B and 3C illustrate embodiments of the probe tip which can be used, for example, with the apparatus shown in FIG. 3A.
Figure 3C:
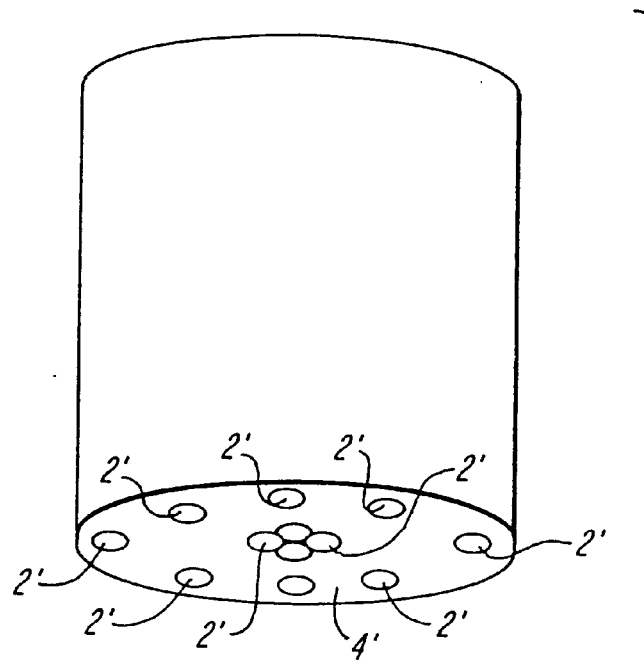
Figure 3C:
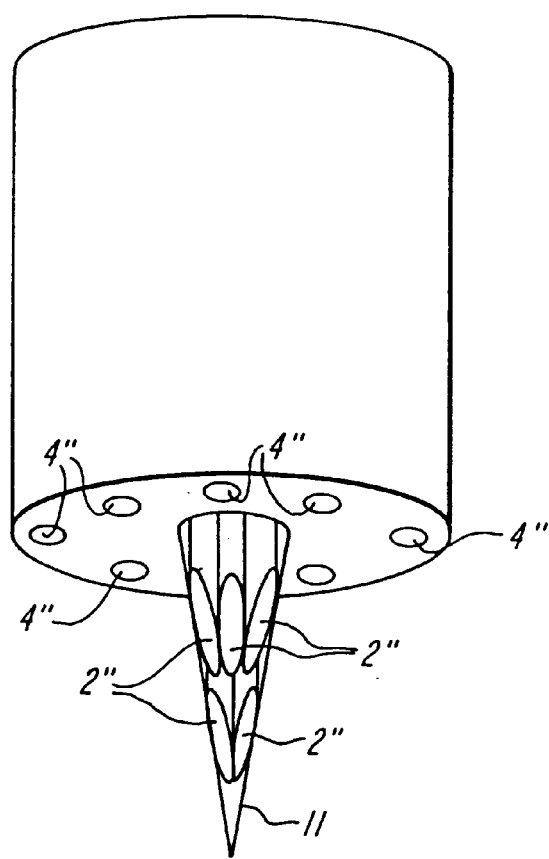

The protective optical shield mechanically displaces the sample into which it is "pushed" and also protects the fiber(s) from the sample contents. The fiber(s) are anchored so that there is an appropriate distance between the output end of the fiber(s) and the tip of the shield. The catheter and shield are sealed watertight, preventing fluid from coming into contact with the internal components. The intervening space may be filled with fluid, or optical surfaces may be optically contacted, or they may be anti-reflection coated to reduce Fresnel reflections and maximize transmitted light. FIG. 3B illustrates other embodiments of the probe, which can be arranged for operation in a transflectance mode, transmission mode or reflectance mode. These embodiments, while illustrating the placement of a detector at the sample interface, can be practiced with fiber optic returns placed in similar location so that the detector can be located distal to the sample. For example, FIG. 3C illustrates illustrative embodiments of probe head assemblies for transflectance and transmission modes. For instance, in the transflectance mode, optical fibers (2') conduct optical energy to the sample, and optical fibers (4') return optical energy to the detector which has been transflected by the sample. Similarly, in the transmission mode, optical fibers (2"), which can be protectively covered with transparent sheath, irradiated the sample from within, while optical fibers (4") return light which has been transmitted through the sample to the detector. In a preferred embodiment of the latter, where multiple optical fibers are used, the fiber bundle can be sheathed, e.g. by a protective transparent cover (11), in a needle-like arrangement to provide for relative ease in puncturing the surface of the sample. Alternatively, the optical cables can truncated at a conical lens which provides for dispersive, e.g. Lambertian, irradiation within the sample and needle-like puncturing abilities.

The detector array (30), e.g. a photodetector, detects light reflected from the sample which passes back through the fiber optic bundle (15) along the afferent fibers (4) of fiber optic bundle (15). The detector array (30) subsequently converts the reflected light into electrical signals having magnitudes indicative of the intensity of the reflected light at each wavelength and transmits the converted signals to the reflection comparator means (40). In one embodiment, the detector array includes a dispersive frequency analyzer, such as a monochrometer, which is used to separate the reflected radiation into its constituent wavelengths. The monochrometer may be either a grating or filter monochrometer. Also, depending on the desired resolution, a single, double, or triple monochrometer may be used. In a simple practical application, the dispersive frequency analyzer may be a monochrometer set so that a predetermined wavelength will be captured. Alternatively, the frequency analyzer component of the detector array (30) may be comprised of an interferometer. An example of a suitable interferometer is a Michelson interferometer, which scans the infrared spectrum. If an interferometer is used, a data processing device (not shown) is in communication with detector array (30) for achieving the Fourier transform analysis, e.g. is part of the reflection comparator means (40).

The reflection comparator means (40) receives the electrical signals representing the output of detector (30) and derives a reflectance ratio for at least two of the wavelengths transmitted. The comparator then compares the calculated reflectance ratio with predetermined values to determine the presence of fatty acid oxidation products. The reflection comparator means (30) can therefore essentially be a data processor which may be a fairly sophisticated device, such as a computer, or may be simply a means for providing an output so that the signal from detector electronics may be compared to a reference.

The output of reflection comparator means (40) is preferably connected to a display which may be in the form of a digital or analog meter or a light or buzzer which is activated when a difference in the signal exceeds a predetermined threshold. The operation of the apparatus (1) can vary in complexity according to the application and the needs of the user. For example, in relatively sophisticated applications, a spectrum of scattered radiation can be obtained and specific features of multiple peaks, e.g. position, intensity, and profile, used to reveal information about the oxidation state of the sample. On the other hand, a simple application might merely compare the intensity of the scattered radiation at a single wavelength to a reference value.

In practice, the probe signals received from a known nondecayed sample (e.g. a standard control) are preferably balanced to zero so that any change in the ratio of two or more signals will produce an unbalanced condition or a voltage signal in the reflection comparator means (40). This allows the threshold value for an indicator light or buzzer. The standardized signals can be adjusted to zero by any known means such as by adjusting the base voltages of the photodetectors or adding the necessary circuitry to permit adjustment of electronic circuit in reflection comparator means (40).

A similar apparatus can be used to perform Raman and Brillouin spectroscopy in order to detect fatty acid oxidation intermediates. In an illustrative embodiment, a nearinfrared laser is used as the illumination source (20) to irradiate the sample of material to be analyzed. Optical fibers (2) transmit incident radiation from a near-infrared radiation source to the sample, and fibers (4) transmit Raman and Brillouin scattered radiation from the sample to the detector array (30).

Another aspect of the present invention concerns the discovery of a novel intermediate in the oxidative degradation of fatty acids. The intermediate is a conjugated diketone structure represented by the general formula:

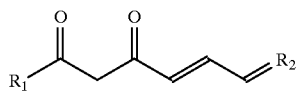

wherein $R_1$ and $R_2$ each independently represents a substituted or unsubstituted $C_1$–$C_{19}$ aliphatic group. For instance, the hydrocarbon backbone of the aliphatic group can contain heteroatoms, such as oxygen or sulphur, in place of methylene groups (see, for example, U.S. Pat. No. 5,082,967), and/or the hydrocarbon backbone may be substituted, e.g. methylene protons replaced, with, for example, a halogen, a hydroxyl, an alkoxyl, a thiol, a phosphoryl, an amino, or a nitro group. Furthermore, each of $R_1$ or $R_2$ can be terminated by a COOH moiety, a lipid head group such as a glycerol moiety, a phosphoglycerol, a diacylglycerol, a phosphatidyl group, or a sphingomyelin. Other head groups include acylated alkanolamines, such as used in low calorie fat mimetics in edible materials (see, for example, U.S. Pat. No. 5,190.783).

Figure 2:
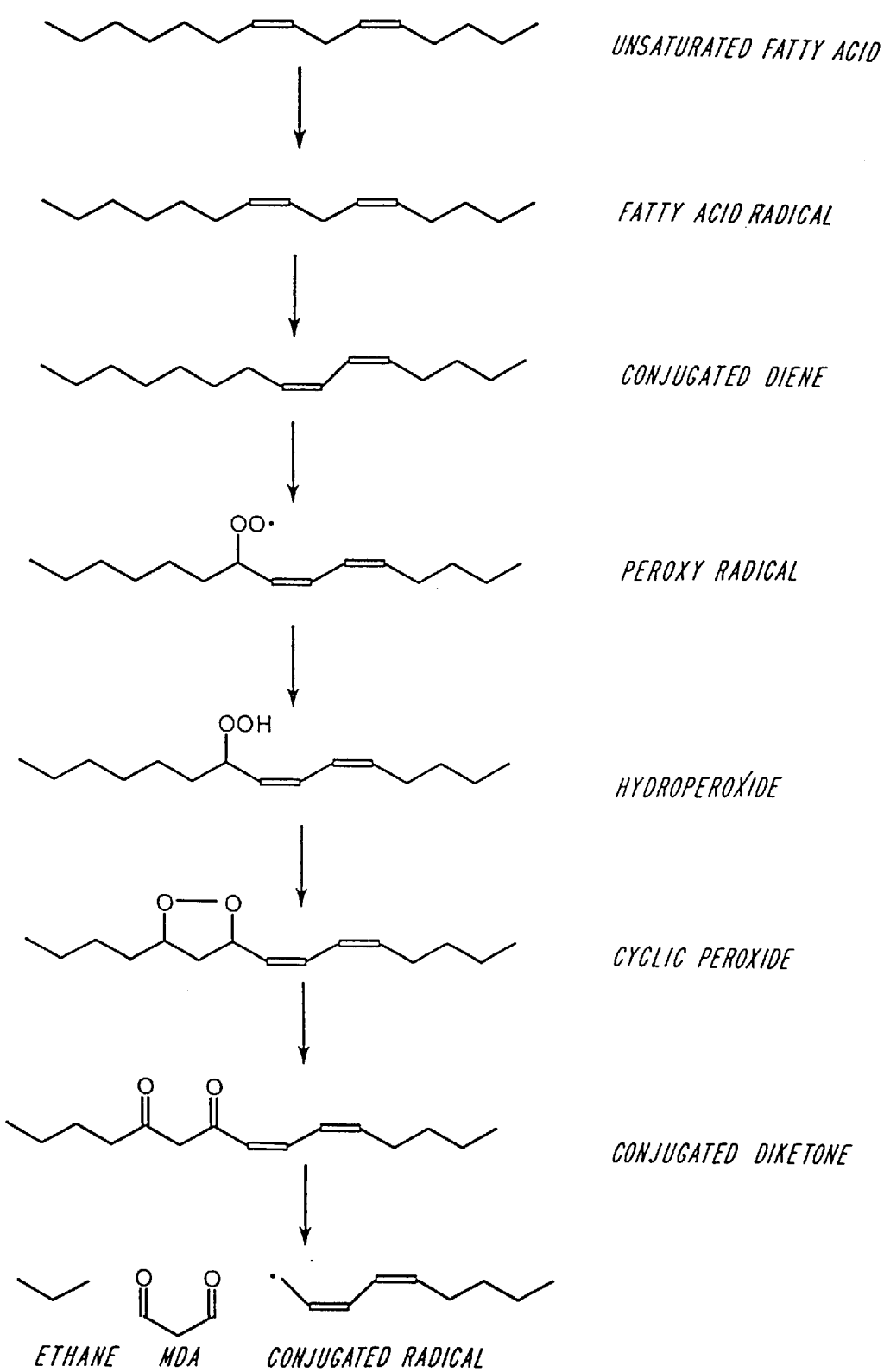
FIG. 2 shows an example of the oxidative pathway of an exemplary unsaturated hydrocarbon which includes a conjugated diketone intermediate.

An illustrative oxidative pathway giving rise to this intermediate is shown in FIG. 2, and data supporting the existence of the conjugated diketone is provided in Example 1. Moreover, in addition to establishing the conjugated diketone as a reaction intermediate of fatty acid peroxidation, it has also been observed that the presence of the intermediate is quantitatively correlated with the level of fatty acid oxidation. Therefore, by quantitatively or semi-quantitatively detecting the presence of the conjugated diketal intermediate, the degree of oxidation of a lipid sample can be determined. In an exemplary embodiment, the level of conjugated diketal intermediates can be determined in a foodstuff, such as fish or meat, in order to ascertain its degree of freshness and/or spoilage.

With respect to the novel conjugated diketal intermediate, the invention generally contemplates a number of methods which can be used to detect and/or quantitate its presence in a sample. These methods include—in addition to the spectroscopic methods described above for lipid oxidation products in general—thin layer chromatography (TLC), spectrophotometric methods, mass spectrometry (MS), nuclear magnetic resonance spectrometry (NMR), electron spin resonance spectrometry, gas chromatography (GC), liquid chromatography (LC), wet chemistry methods and combinations thereof. Many of these methods can be used to detect the presence of and/or quantitate conjugated diketal hydrocarbons in both non-living samples and in tissues present in a subject. Preferably, the spectrophotometric methods described above are used to detect conjugated diketal hydrocarbons in a tissue of a subject (i.e., in vivo).

Methods exist in which a sample containing lipids can be subjected to a chromatographic step to separate the lipids into lipid classes (see, for example, U.S. Pat. No. 4,900,680). These lipid classes can then be reacted with an agent to determine the presence of a conjugated diketone structure and/or can be subjected to chromatographic or spectrophotometric analysis.

Mass spectrometry provides yet another method of detecting and/or quantitating the amount of a conjugated diketal in a sample. A mass spectrometer can bombard the substance under investigation with an electron beam and quantitatively records the result as a spectrum of positive ion fragments. This record is a mass spectrum. Separation of the positive ion fragments is on the basis of mass (strictly, mass/charge, but the majority of ions are singly charged).

Mass spectra are routinely obtained at an electron beam energy of 70 electron volts. The simplest event that occurs is the removal of a single electron from the molecule in the gas phase by an electron of the electron beam to form a molecular ion, which is a radical cation. Many of these molecular ions disintegrate in 10-10 to 10-3 second to give, in the simplest case, a positively charged fragment and a radical. A number of fragment ions are thus formed, and each of these can cleave to yield smaller fragments.

If some of the molecular (parent) ions remain intact long enough (about 10-6 seconds) to reach the detector, a molecular ion peak is seen. It is important to recognize the molecular ion peak because this gives the molecular weight of the compound. With unit resolution, this molecular weight is the molecular weight to the nearest whole number, and not merely the approximation obtained by all other molecular weight determinations.

A mass spectrum is a presentation of the masses of the positively charged fragments (including the molecular ion)

versus their relative concentrations. The most intense peak in the spectrum, called the base peak, is assigned a value of 100%, and the intensities (height X sensitivity factor) of the other peaks, including the molecular ion peak, are reported as percentages of the base peak. Of course, the molecular ion peak may sometimes be the base peak. Based on this information, an analysis can be made to determine the relative ratios of conjugated diketones in a sample based on its molecular weight and relative intensity to the base peak (typically the unoxidized form of the fatty acid in the sample).

In yet another embodiment of the subject assay, nuclear magnetic resonance (NMR) spectrometry can be used to detect the conjugated diketone intermediate. NMR is basically another form of absorption spectrometry, akin to infrared or ultraviolet spectrometry. Under appropriate conditions, a sample can absorb electromagnetic radiation in the radio-frequency region at frequencies governed by the characteristics of the sample. In general, H1 NMR spectra can be acquired from any sample without need of enrichment. However, such spectra are only likely to be useful in the subject assay where the sample is a relatively pure fatty acid preparation. However, the different relaxation times for protons of fatty acids versus other molecules in the sample can be exploited in more complicated systems, as can the use of 2-D and 3-D NMR techniques (e.g. NOE effects, J coupling effects, HMQC, etc.) to filter out uninteresting signals.

In some instances, it will be preferable to separate the various constituents of a sample from one another prior to analysis. However, such separations can also be used to detect and/or quantitate conjugated diketal hydrocarbons.

One of the most widely used means of performing analytical separations is chromatography. Chromatography encompasses a diverse group of separation methods that allows fro the separation, isolation, and identification of closely related components of complex mixtures. All of these methods make use of a stationary phase and a mobile phase. Components of a mixture are carried through the stationary phase by the flow of the mobile phase; separations are based on differences in migration rates among the sample components.

Chromatography includes column and planar chromatography. Column chromatography, e.g., gas chromatography, e.g., liquid chromatography, e.g., high pressure liquid chromatography, refers to methods in which the stationary phase is contained in a tube. The mobile phase, which can be a liquid or a gas, is then forced through the stationary phase under pressure or allowed to percolate through it by gravity. In planar chromatography, e.g., thin layer chromatography, the stationary phase can be supported on a flat plate or can be a piece of paper. Here, the mobile phase moves through the stationary phase either by capillary action or under the influence of gravity. In either type of chromatography, the stationary phase can be a finely divided solid or an immobilized liquid that is immiscible with the mobile phase.

The conjugated diketal hydrocarbon can also be detected by chemical means (i.e., application of a chemical substance to the sample and detecting a change in color or precipitate indicating the presence of the conjugated diketal structure). Several chemical tests are available to detect the presence of a ketone in a sample. For example, when a sample treated with hydroxylamine develops a yellow to red color, this can indicate the presence of a ketone structure. As the other isolated oxidation intermediates do not have ketone structures, this can be used to identify the presence of the newly isolated intermediate. Other chemical agents include 2,4-dinitrophenylhydrazine which also turns the sample yellow to red and the combination of mercuric chloride and sodium ethoxide which generates a white to cream color precipitate. Preferably, wet chemical methods such as these are performed on samples removed from a subject or on non-living tissue or samples.

EXEMPLIFICATION

The invention now being generally described, it will be more readily understood by reference to the following examples which are included merely for purposes of illustration of certain aspects and embodiments of the present invention, and are not intended to limit the invention.

EXAMPLE 1

Identification of a Conjugated Diketone Intermediate

Figure 6A:
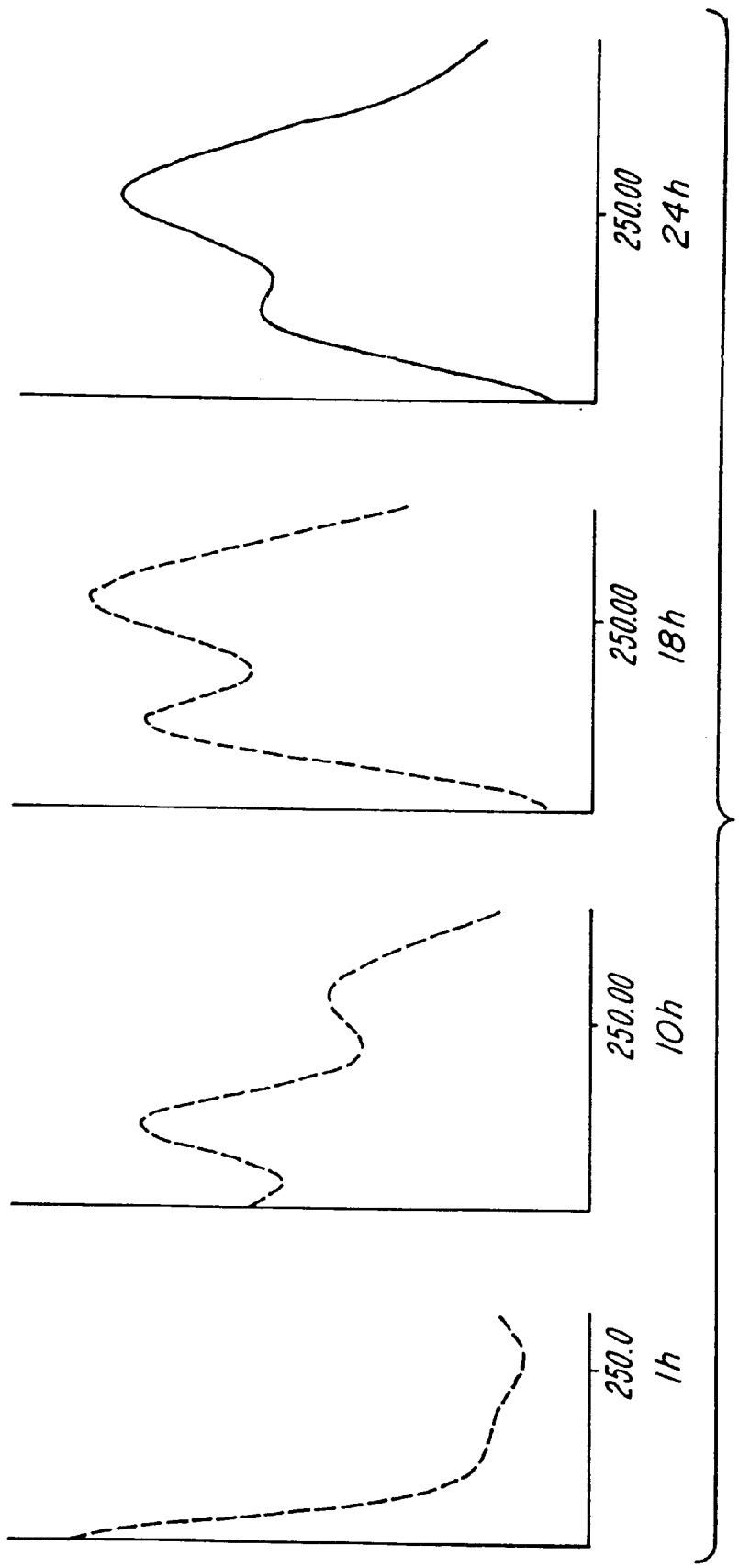
FIG. 6A illustrates the results of a time course oxidation study of an 18:2 fatty acid-containing triglyceride.

By analysis of decomposition products, and consideration of known intermediates in the peroxidation of polyunsaturates (e.g., as shown in FIG. 1A), it was postulated that a previously unidentified intermediate, namely a conjugated diketone intermediate, existed in the oxidation pathway. Among the experiments accomplished to determine if such a conjugated diketone existed, a spectral time course study was performed following the oxidation of an unsaturated fatty acid and the equivalent hydroxylated fatty acid. FIG. 6A illustrates the results of a time course oxidation study of an 18:2 fatty acid-containing triglyceride (1,2,3-Tri-[9,12-octadecadienoyl]glycerol; Sigma Chemical Company). A sample of the triglyceride was provided in a quartz cuvette and incubated at 24° C. The absorption spectra of the sample in the wavelength range of approximately 200 to 300 nm was obtained using a Shimatdzu CS-9000 spectrodensitomiter, at time intervals of 1, 10, 18 and 24 hours. As that figure indicates, there is a steady increase in the concentration of an apparent oxidation intermediate which is manifest in the spectrum as a peak centered at about 260 nm, the intensity of which is evidently a function of the incubation time at 24° C.

Figure 6B:
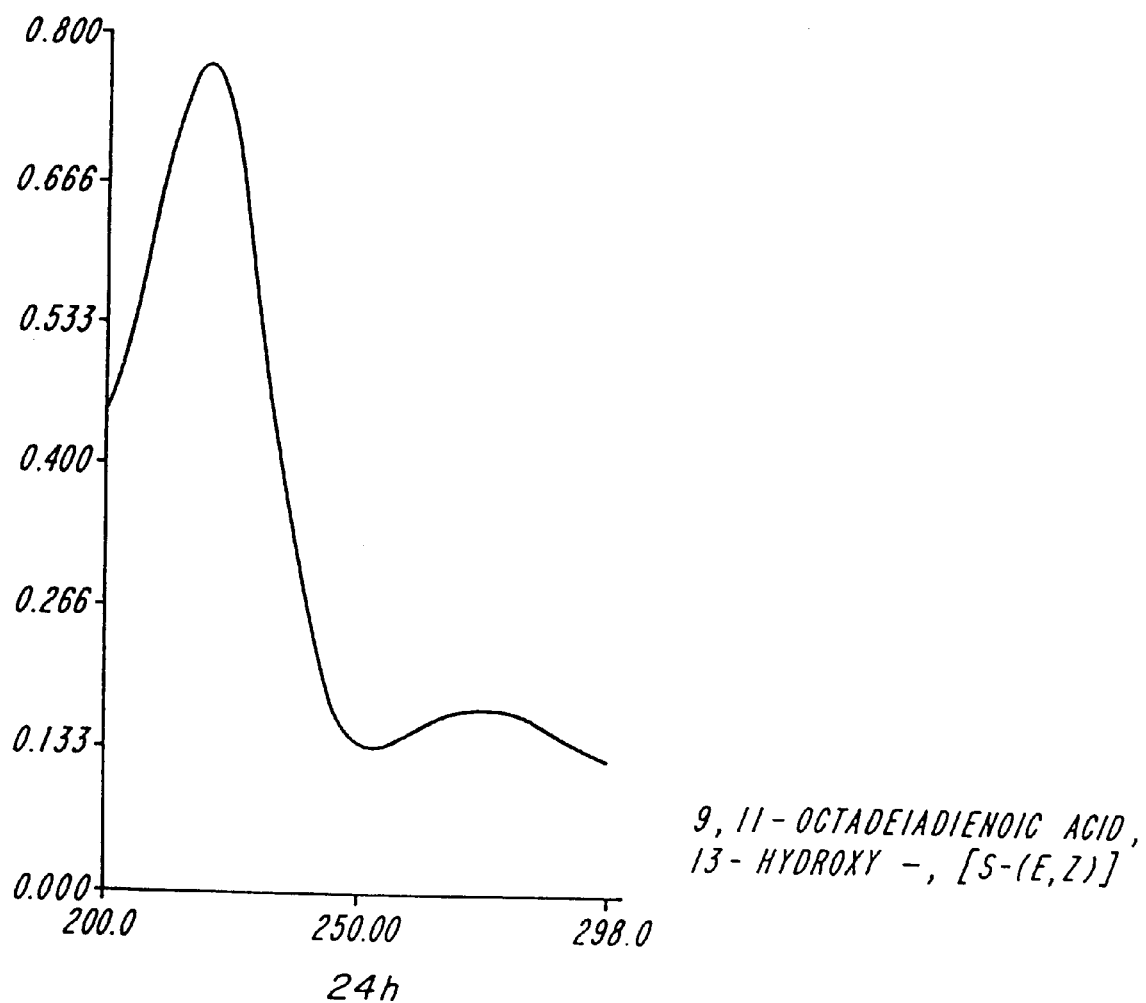
FIG. 6B is the spectra of an 18:2 hydroxylated conjugated diene ([13S]-HODE) incubated for 24 hours at 24° C.

By comparison, the spectrum shown in FIG. 6B of the 18:2 hydroxylated conjugated diene ([13S]-HODE; Cayman Chemical Company) incubated for 24 hours at 24° C. indicates that, despite the presence of two conjugated double bonds, the same intermediate is apparently not formed. It is asserted that the reduction of a hydroperoxide group, ROOH, to an alcohol, ROH, would prevent the formation of a cyclic hydroperoxide and therefore prevent further oxidation of a conjugated diene to a diketone intermediate. Accordingly, the hydroxylated conjugated diene [13S]-HODE, which is in effect the equivalent to the product of reducing a lipid hydroperoxide intermediate to an alcohol, would be incapable of forming the postulated conjugated diketone. The lack of an apparent intermediate in the subject time course study of [13S]-HODE supports the contention that the conjugated diketone is an intermediate downstream of the hydroperoxide intermediate in the oxidation pathway for polyunsaturates. Moreover, the spectra of FIG. 6A further provide a useful UV/VIS absorption band (~260 nm) for monitoring oxidation of fatty acids.

EXAMPLE 2

Detection of a Conjugated Diketone Intermediate in a Food Sample

To determine if the conjugated diketone intermediate is useful for monitoring lipid oxidation in a sample of food, the presence of the intermediate was detected at various time points in an aliquot of milk which was incubated at room temperature. Milk is a useful test system in that mere exposure to air at room temperature is sufficient to cause oxidation of polyunsaturated fatty acids in the sample, and results in the milk becoming rancid.

Figure 7A:
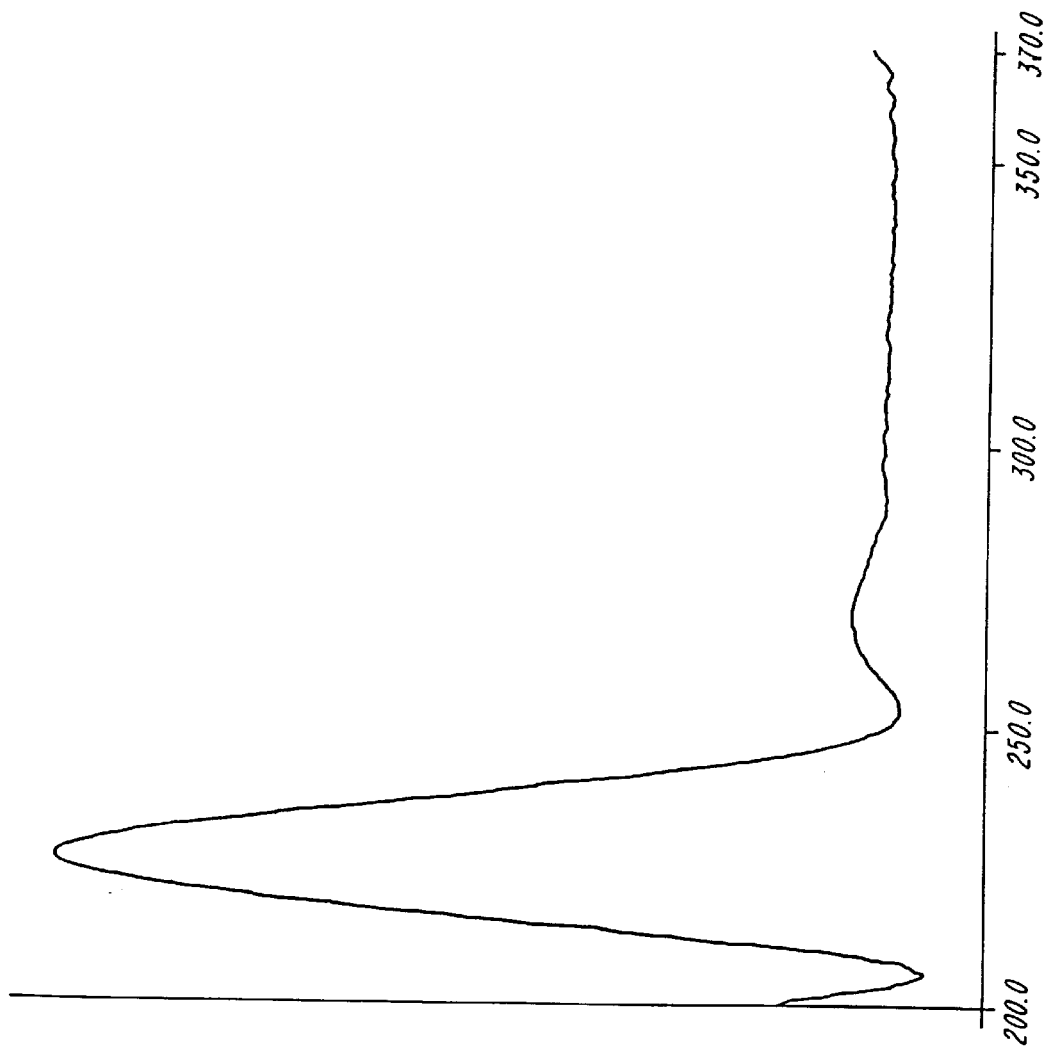
FIGS. 7A and 7B are spectra obtained during a time course study of a sample of milk exposed to air at room temperature. The spectra in FIG. 7A is taken after 12 hours, while the spectra shown in FIG. 7B were taken at 24 hours (each spectra representing a different amount of milk used in the emulsion step of Example 2).
Figure 7B:
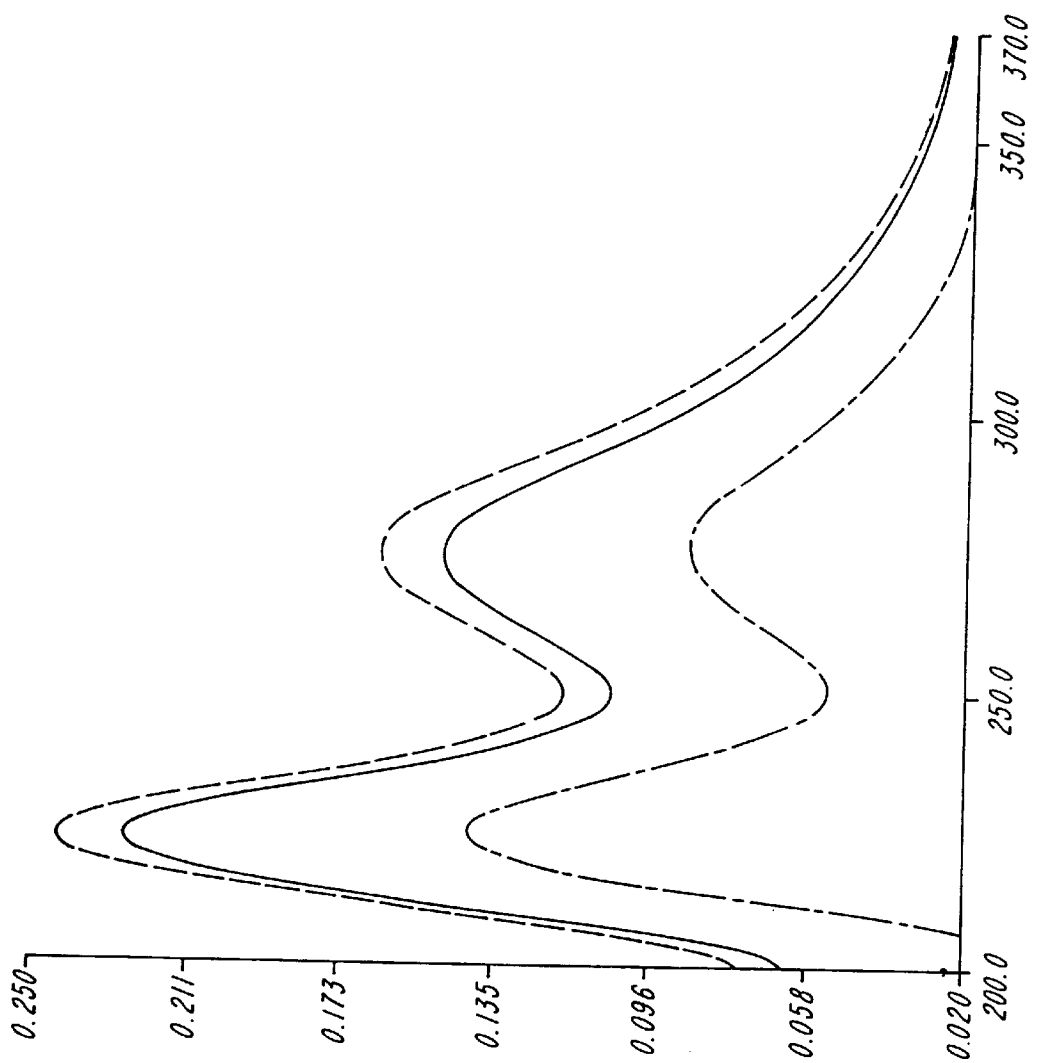
Figure 8:
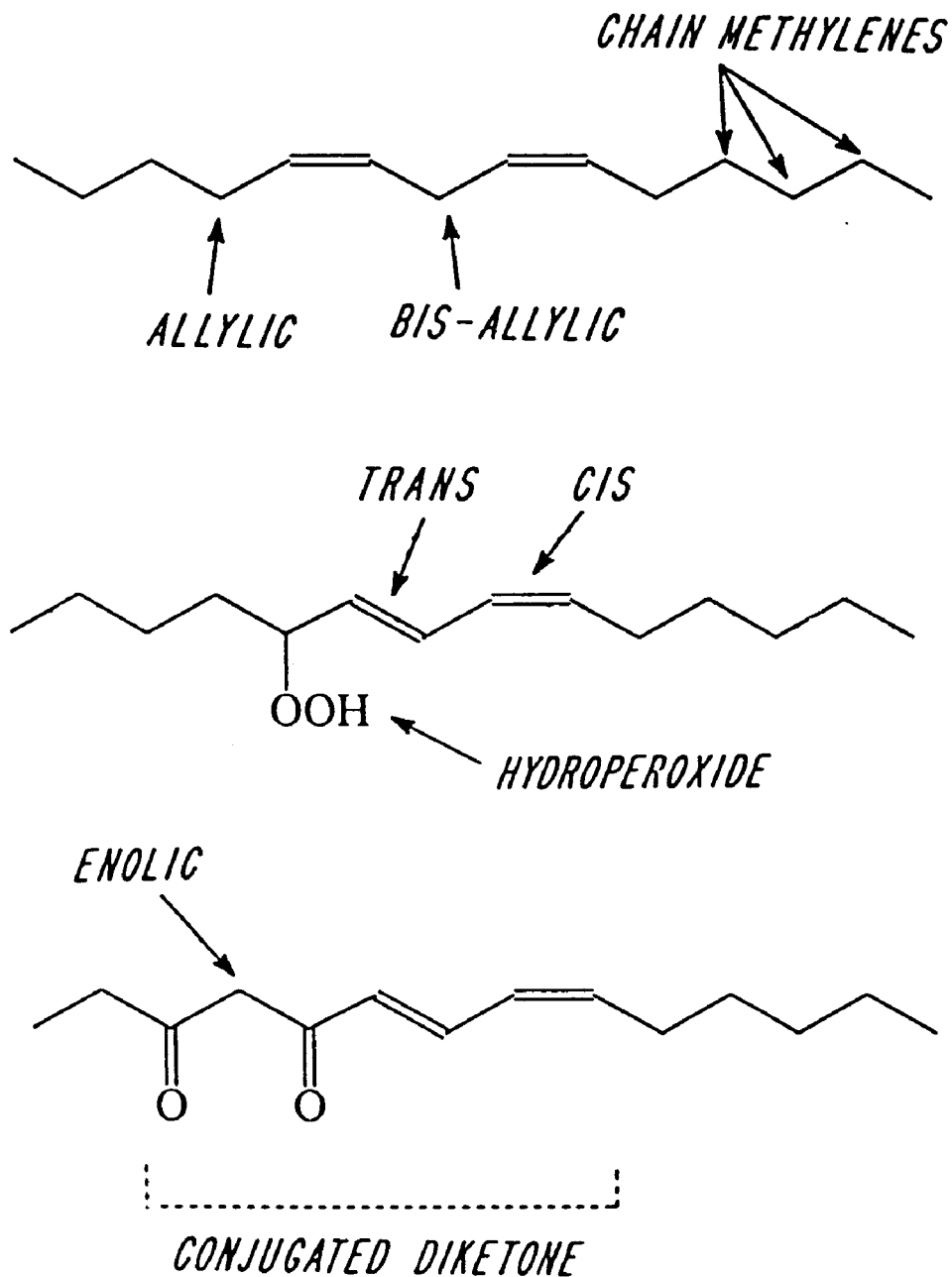
FIG. 8 illustrates the nomenclature of certain chemical features refered to throughout the application.

Briefly, the experiment was carried out as follows. Milk samples from each of the different time points were emulsified in 6 volumes chloroform-methanol (2:1, v/v), and centrifuged at 600 g for 3 minutes. The organic phase (lower phase) was isolated, evaporated to dryness, and resuspended in 100 µl choroform-methanol (1:1, v/v). Aliquots of 4gl each of the lipid suspension were spoted onto Whatman silica gel HP-K plates (5 cm×5 cm). The plates were predeveloped in chloroform-methanol (1:1, v/v) followed by development with chloroform-ethanol-triethylamine-water (30:34:30:8, v/v/v/v) for 3 cm, throughly dried and further developed in hexane-diethyl ether (50:5, v/v) to the top of the plate. The developed chromatograms were again dried, and spectra of the triglyceride fraction were obtained directly from the TLC plates using a Shimatdzu CS-9000 spectrodensitomiter. As FIG. 7A illustrate, the conjugated diketone is detectable by the end of the first day as a peak at approximately 270–275 nm. However, as FIG. 7b demonstrates, subsequent oxidation of the sample results in a more significant absorbance peak due to conjugated diketone intermediated of unsaturated fatty acids in the sample. Thus, the presence of the conjugated diketone intermediate is indicative of milk spoilage, and presumably of taste as well. Consequently, detection of the conjugated diketone intermediate can be used to determine shelf-life of refrigerated milk by carrying out an analogous time course study at 4° C.

EXAMPLE 3

Determination of Fatty Acid Oxidation in Fish Meat by Near Infrared Detection

FIGS. 4A–4C illustrate the use of the subject method for determining the freshness of a sample of fish meat. FIGS. 4A–4C are near-IR spectra obtained from an Atlantic salmon specimen over a period of 12 hours. In particular, FIG. 4A corresponds to the fresh specimen of salmon obtained from a local supermarket; FIG. 4B is a spectrum of the salmon meat after it had been incubated at room temperature for 1h; and FIG. 4C is a spectrum of the sample after incubation at room temperature for 12h. Each of the near-IR spectra were acquired using a Monolite Spectrum Analyzer Model 6100 instrument and low OH silica visible/infrared fiber optics from FiberGuide Industries.

As shown in these spectra, a peak is evident at 2115 nm and, with reference to Table 1 above, can be assigned as the combination band for a stretching of a doubly allylic proton. In the fresh salmon sample (FIG. 4A) the peak is present and, relative to the oxidized samples (FIGS. 4B and 4C), is most intense. However, during oxidation, the vinyl methylenes are lost upon conjugation of double bonds, as well as converted to hydroperoxides. Indeed, as is apparent from the spectra of FIG. 4B and 4C, the 2115 nm peak is diminished over time as oxidation of the sample occurs. Consequently, comparison of the intensity of this peak between samples can be used correlatatively to establish the freshness (or lack thereof) of a particular sample, and can also be related to the taste of the meat.

Generally, detection and correlation of a chemical feature such as the bis-allylic proton will require the use of a reference wavelength to standardize data obtained from one sample to the next. Accordingly, the ratio of absorbance at a reference wavelength (e.g. a wavelength insensitive to the concentration of fatty acid oxidants) to absorbance at a sample wavelength can be used to correlate the freshness of the sample. For instance, the ratio of absorbance at a sample wavelength of 2115 nm peak and at a reference wavelength of 2138 nm peak (relatively insensitive to oxidation), can be used to determine the oxidative state of the sample by comparing that ratio determined for the sample with ratios determined in known standards. Known standards can include fresh samples, such as the fresh fish meat used to generate the spectra of FIG. 4A, as well as samples which have been allowed to oxidize under defined conditions. The correlation between taste or freshness and oxidation of the meat as detected by the present assay can also be used to generate a data set typical for predicting oxidation of other samples of that food, and from which values measured in unknown samples can be compared such that remaining shelf-life, freshness or expected taste may be interpolated.

EXAMPLE 4

Determination of Fatty Acid Oxidation in Fish Meat by Raman Detection

Figure 5B:
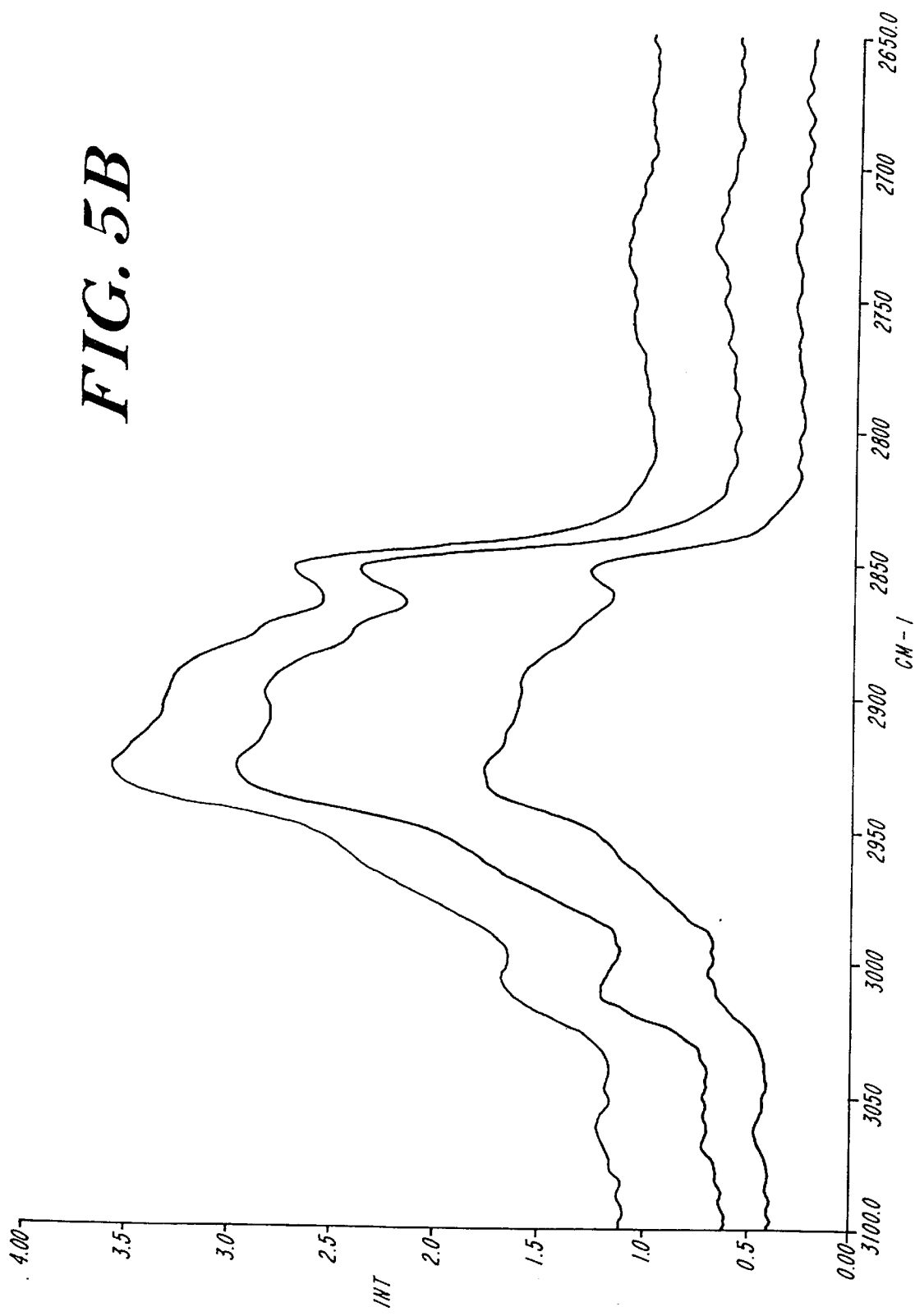

In similar fashion, the suitablity of Raman spectroscopy for observing the oxidation of a food sample was ascertained. FIGS. 5A and 5B are Fourier Transform (FT) Raman spectra of a sample of blue fish meat obtained from a local market. Each of the FT-Raman spectra were acquired with a Perkin-Elmer Model 1710 FTIR instrument using an excitation wavelength of 1064 nm from a $Nd^{3+}$:YAG laser.

In FIG. 5A, the lower spectrum corresponds to a fresh specimen of blue fish with the skin layer removed, while the upper spectrum corresponds to the same specimen with the skin still on. Comparison of the two spectra reveals that very few features of the spectra are different between the sample with the skin and without, indicating that the skin is, in effect, optically pierced by the excitation beam. Consequently, the oxidative state of the sample can be determined without any need to remove (e.g., destroy) the skin of the sample.

To determine the oxidative state of the sample, it was found that the bis-allylic proton, detectable at approximately 3000 $cm^{-1}$ by Raman spectroscopy, was a suitable indicator. As oxidation progresses, the C-H stretching signal decreases as vinyl methylenes are lost from the sample due to conversion to oxidative products. A convenient internal reference wavelength is 1450 $cm^{-1}$ (see FIG. 5A), which corresponds to a vibrational mode of the C=C bond. In FIG. 5B, the middle spectrum corresponds to the fresh specimen of blue fish; the upper spectrum corresponds to the sample after 1h incubation at room temperature; and the lower spectrum to the sample incubated at room temperature for 12h. Inspection of the three spectra reveals that the intensity of the vinyl proton band at 3000 $cm^{-1}$ is diminished as the sample is allowed to oxidize. The ratio of the intensity of the 3000 $cm^{-1}$ peak to the 1450 $cm^{-1}$ peak (not shown) was found to decrease as the sample was oxidized. As above, standardized Raman data can be collected for defined specimens of meat and other foodstuffs, providing a model from which freshness, shelf-life or taste can be predicted from measurements taken of an sample pf unknown oxidation.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for determining a level of oxidative stress of a tissue sample, comprising:

(i) irradiating the sample with electromagnetic radiation at a plurality of wavelengths including a reference wavelength and a sample wavelength, wherein absorption of light at the sample wavelength varies with a state of oxidation of unsaturated fatty acids in the tissue sample, and the reference wavelength is sufficiently removed from the sample wavelength so that absorption of light at the reference wavelength is substantially insensitive to concentration of oxidized unsaturated fatty acids in the tissue sample;

(ii) spectrophotometrically detecting radiation absorbed or scattered by the sample at each of the sample and reference wavelengths, wherein absorbance at the sample wavelength by the tissue sample correlates with the state of oxidation of unsaturated fatty acids in the tissue sample;

(iii) determining a ratio of absorbance at the sample wavelength to absorbance at the reference wavelength for the tissue sample, said ratio being correlated to an oxidative stress level of the tissue;

(iv) ascertaining the oxidative stresses level of the tissue by comparing the ratio determined in (iii) with a predetermined ratio value measured in one or more standard tissue samples of known oxidative stress levels.

2. The method of claim 1, wherein the spectrophotometric detection of radiation absorbed or scattered by the sample is performed using a method selected from a group consisting of ultraviolet-visible spectrometry, infrared spectrometry, and Ramam spectrometry.

3. The method of claim 1, wherein the tissue comprises myocardial tissue and the oxidative stress level is predictive of myocardial ischemia.

4. The method of claim 1, wherein the oxidative stress level is predictive of artherosclerosis or risk of artherosclerosis.

5. The method of claim 1, wherein the tissue comprises cerebral-spinal tissue and the oxidative stress level is predictive of brain ischemia.

6. The method of claim 1, wherein the tissue comprises hepatic tissue and the oxidative stress level is predictive of hepatotoxicity or risk of hepatotoxicity.

7. The method of claim 1, wherein the tissue comprises hyperplastic or neoplastic cells, and the oxidative stress level of the tissue is predictive of the presence of tumor cells.

* * * * *